(12) United States Patent
Buechler et al.

(10) Patent No.: US 6,392,894 B1
(45) Date of Patent: May 21, 2002

(54) MEDIA CARRIER FOR AN ASSAY DEVICE

(75) Inventors: Kenneth F. Buechler, San Diego; Joseph M Anderberg; Paul H. McPherson, both of Encinitas, all of CA (US)

(73) Assignee: Biosite Incorporated, San Diego, CA (US)

( * ) Notice: Subject to any disclaimer, the term of this patent is extended or adjusted under 35 U.S.C. 154(b) by 0 days.

(21) Appl. No.: 09/545,699

(22) Filed: Apr. 6, 2000

Related U.S. Application Data

(63) Continuation of application No. 09/003,006, filed on Jan. 5, 1998, now Pat. No. 6,074,616.

(51) Int. Cl.[7] .................................................. H05K 5/00
(52) U.S. Cl. ...................... 361/752; 361/760; 361/761; 361/748; 361/737; 439/76.1; 235/486; 235/475; 422/104; 422/67; 422/99
(58) Field of Search ................................ 361/752, 800, 361/816, 818, 760, 761, 748, 814; 439/76.1; 422/104, 67, 99; 235/475, 486

(56) References Cited

U.S. PATENT DOCUMENTS

| | | | |
|---|---|---|---|
| 4,099,886 A | 7/1978 | Oliveira | |
| 4,326,125 A | 4/1982 | Flies | 235/443 |
| 5,028,535 A | 7/1991 | Buechler et al. | 435/7.1 |
| 5,053,199 A | 10/1991 | Keiser et al. | |
| 5,089,391 A | 2/1992 | Buechler et al. | 435/7.1 |
| 5,143,852 A | 9/1992 | Valkirs et al. | 436/501 |
| 5,276,317 A | 1/1994 | Ozouf et al. | 235/486 |
| 5,289,345 A | * 2/1994 | Corradetti et al. | 361/752 |
| 5,366,609 A | 11/1994 | White et al. | 204/403 |
| 5,458,852 A | 10/1995 | Buechler | 422/58 |
| 5,480,792 A | 1/1996 | Buechler et al. | 435/6 |
| 5,499,162 A | 3/1996 | Bartuska et al. | 361/737 |
| 5,519,577 A | 5/1996 | Dudas et al. | 361/737 |
| 5,525,524 A | 6/1996 | Buechler et al. | 436/518 |
| 5,635,364 A | 6/1997 | Clark et al. | |
| 5,696,369 A | 12/1997 | Watanabe | 235/454 |
| 5,739,515 A | 4/1998 | Takemura | 235/441 |
| 5,757,622 A | 5/1998 | Tanaka et al. | 361/737 |
| 5,877,488 A | 3/1999 | Klatt et al. | 235/486 |
| 5,906,516 A | 5/1999 | Sato et al. | 439/630 |

FOREIGN PATENT DOCUMENTS

EP 0571225 A2 11/1993

* cited by examiner

*Primary Examiner*—David Martin
*Assistant Examiner*—Thanh Y. Tran
(74) *Attorney, Agent, or Firm*—Foley & Lardner

(57) ABSTRACT

A fluorometer for sensing the fluorescence of a sample utilizes an optical energy source for exciting a sample to be tested and an optical energy detector for detecting the emitted energy from the excited sample. Drive electronics are used for positioning the sample with respect to the optical components allowing a plurality of sample regions to be tested. A processor is utilized to control the operation of the test in accordance with test instructions and for processing the emitted energy detected from the sample to determine test results. A ROM chip socket accepts a plurality of ROM chips, wherein each ROM chip stores test data sets for one or more test types to be performed. ROM chips can be swapped to allow the fluorometer to be configured and reconfigured to perform a plurality of different tests. A communications interface facilitates the sharing of test information between the fluorometer and external entities.

8 Claims, 13 Drawing Sheets

MEDIA CARRIER FOR AN ASSAY DEVICE

RELATED APPLICATIONS

This is a continuation of application Ser. No. 09/003,066, filed Jan. 5, 1998, now U.S. Pat. No. 6,074,616.

The present application is related to copending U.S. patent applications Ser. No. 09/003,090 titled "Immunoassay Fluorometer," and Ser. No. 09/712,615 titled "Methods for Monitoring the Status of Assays and Immunoassays," each of which are filed concurrently herewith and each of which are incorporated herein by reference in their entirety.

BACKGROUND OF THE INVENTION

1. Field of the Invention

The present invention relates generally to fluorometers, and more particularly to a system and method for performing automated fluorescent measurements.

2. Related Art

Conventional medical devices used to perform fluorescent readings are large, dedicated machines. Typical fluorometers are bench-top devices which are not easily transported from location to location. Additionally, conventional fluorometers are not easily capable of being programmed by the user or otherwise configured by the user to perform a plurality of different types of tests. Instead, the conventional fluorometer is factory-programmed to perform a predefined test protocol.

To perform a test using a conventional fluorometer, a laboratory technician obtains a sample. The sample can be a biological fluid, such as blood, serum, plasma, urine, a fecal extract and the like or it can be an environmental sample, such as water, a ground extract, a chemical and the like or it can be an extract of a food product. In the case of a blood sample, the blood is first separated into plasma or serum, which becomes the sample, and cellular fractions using a centrifuge. The sample is then generally deposited into a small test tube that is inserted into the fluorometer. Because the conventional fluorometer can accept several samples, the technician enters an identification of the sample and the location of the test tube into the fluorometer.

Once one or more test tubes containing samples are positioned in the fluorometer, the test begins. Contemporary fluorometers use robotics to pipet the sample and the reagents and to position one or more optical sensors by the sample to obtain the necessary readings. The readings are recorded along with the associated test-tube location designations. The location designation is used to identify the sample.

SUMMARY OF THE INVENTION

The present invention provides a system and method for performing automated fluorometry. According to the invention, a fluorometer is provided which includes functionality to provide enhanced operational characteristics for the measurement of analytes in a sample. The system and method has particular importance as a laboratory or non-laboratory tool for rapidly and conveniently measuring analytes by skilled laboratorian or by individuals who are unskilled as laboratorians. According to one or more embodiments of the invention, the fluorometer can include an optical block, a removable storage medium, an internal processor, a communications interface, and internal data storage.

The system and method generally comprises the fluorometer and a testing or assay device. The assay device is used in conjunction with the fluorometer to achieve a result regarding the concentration or presence of an analyte in a sample. Examples of analytes include chemicals, proteins, peptides, bacteria, viruses, nucleic acids, cellular organelles, cells, receptors and the like. The assay device can include reagents that are necessary for performing an immunological or chemical reaction, such reaction giving rise to a change in fluorescence of the sample that has been treated with the reagents. The reagents can include chemicals, antibodies, peptides, analytes, analyte analogues and these reagents may or may not be coupled to fluorescent labels or to solid phases.

In one embodiment, the removable storage medium is implemented utilizing a ROM chip or other memory device, which can be interfaced to the fluorometer to provide operating instructions as well as calibration curves and control and calibration data. Preferably, the memory device is mounted on a carrier which provides easy insertion and removal such that a plurality of memory devices containing specific sets of data can be easily interchanged. In this manner, the fluorometer can be easily programmed and reprogrammed to perform a variety of tests and calibrations.

Additionally, the removable storage medium can be implemented using a removable medium such as a disk and disk drive. The disk can contain test data sets for one or more types of tests to be performed. The test data sets can include test instructions and calibration curves for the test, as well as other program information and calibration and control information for the instrument.

A communications interface can be included to facilitate communications between the fluorometer and one or more other devices. The communications interface can include a wired and wireless interface to provide direct or networked communications. The communications interface can be used to download test data sets, including, for example, test identifications, test instructions and calibration curves, as well as other program information and calibration and control information. The communications interface can also be used to allow the fluorometer to share processing responsibilities with other devices such as a computer or other processor. Such an interface (wired or wireless) can be implemented, for example, utilizing an RS-232, infrared or modem interface for direct connection, or a network interface for network communications to one or more processors.

In one operational scenario, the communications interface is used to allow a physician or other health care professional at a health care facility (e.g., a doctor's office, clinic, testing center, hospital, or other health care site or facility) to transmit test instructions to the fluorometer with regard to which tests are to be performed for a particular patient. The interface can also be used to forward test results to a health care facility to apprise the health care professional of the results. Results of tests and a catalog of tests performed can be sent to various locations for patient-diagnosis, record-keeping, billing, and other purposes.

In an alternative operational scenario, a patient can perform testing at home, and test results and instructions can be exchanged with a health care facility via the communications interface. In this embodiment, patients who require frequent monitoring can get the necessary tests without traveling to a health care facility each time a test is needed, for example, as may be required by patients taking daily regimens of therapeutic drugs.

In yet another operational scenario, a technician in the field can measure water or ground contamination and transmit the results to a home office via a cellular telephone or other communications medium to inform officials of the progress of a decontamination procedure.

Internal data storage can be used to store program instructions (including test instructions), calibration curves, control and calibration data as well as other data used in the operation of the fluorometer. Internal data storage can also provide register space for operand storage. Internal data storage can be implemented using, for example, RAM or DRAM technology, or other memory technology. Disk or other storage space can be used to supplement the internal data storage, depending on storage cost and access latency tradeoffs. Cache techniques can also be used to optimize performance.

Data storage, either internal or removable, can be used to store test information regarding a test or tests conducted or to be conducted on one or more samples. The test information can include information such as, an identification of the patient and other patient information, a sample identification, an identification of a test or tests performed on the sample, a date and time at which the tests were conducted, test conditions, test results, specific reagent information, such as lot numbers and expiration dates and other pertinent information. The test information can be stored in a record that can be indexed using, for example, the patient identification or other indexing designation.

Various user interfaces can be provided to facilitate user control and to enhance operability of the fluorometer. Input interfaces can include data entry devices such as a keyboard, keypad, touch-screen display, mouse, voice recognition input, or other data entry device. Output interfaces can include a display screen or monitor, printer, speaker or other output device.

The assay mechanism according to one embodiment includes a motorized mechanism for transporting the assay device in the fluorometer. Examples of such a motorized mechanism include, for example, those as described in U.S. Pat. No. 5,458,852 and copending U.S. patent application Ser. No. 08/458,276, titled "Devices For Ligand Receptor Methods," which are incorporated herein by reference. The movement of the assay device in the fluorometer functions to position the diagnostic lane of the device with an optical block so that one or more fluorescent areas or zones of the assay device can be measured. The degree or presence of fluorescence in the diagnostic lane is related to the concentration or presence of analyte in the sample. The optical block can include a light source, detector and optics used to excite the sample as well as to sense the fluorescence of the excited sample. In one embodiment, the sample is disposed on the assay device. The assay mechanism can provide the capability to transport the assay device along the optical block such that fluorescence of one or more of a plurality of zones on the diagnostic lane of the device can be measured. As such, one advantage of the invention according to this embodiment is that enhanced testing algorithms can be utilized, if desired, in measuring the fluorescence of the sample.

An additional advantage of the invention is that the communications interface can be used to allow the fluorometer to be interfaced to networks such as, for example, a hospital or other health care facility network, or other information networks whereby the fluorometer can retrieve data which may be needed to conduct tests and download other data including the test results. Additionally, the communications interface can be used to interface with the fluorometer to a stand alone computer such as, for example, a personal computer or an office or a home office computer. In these configurations, the fluorometer can utilize the processing and peripheral capabilities of the stand alone computer or network resources to supplement its own processing and interface capabilities. In yet another configuration, the fluorometer can interface with an existing instrument that is interfaced to a network, such as, for example, an instrument in a hospital emergency department or critical care unit that dispenses medications for use by the hospital personnel. Interfacing the fluorometer to an existing instrument has advantages in that the interface of the fluorometer to the instrument can be one specific code, whereas the instrument interface code can be varied depending on the location of the instrument, for example, in different hospitals with different software interface codes.

For example, in one embodiment, the fluorometer can be operated as a portable hand-carried piece of test equipment that is used to test samples of blood. The portable, hand-carried unit can then be interfaced to a computer or computer network to upload test results or to simply communicate other data associated with the test and to use the processing power of the computer or computer network to perform some or all of the actual test processing. In yet another example, test data sets or other pertinent information can be downloaded from the outside entity to provide the fluorometer with guidance as to tests to be conducted on a particular sample. This guidance can be in the form of complete test instructions or simply an identification of a test to be performed for which the instructions are stored internally to the fluorometer. In another example, the data communicated to a network can be utilized in real time to diagnose and treat acute care patients.

Yet another feature of the invention is that it provides an encoded tag on the assay device such as, for example, a bar code label or magnetic strip to allow sample, test or reagent information to be encoded. Sample information can include, for example, an identification of the sample and sample type, an identification of the patient from which the sample was drawn, an indication of the test or tests to be performed for the sample, as well as other data, as desired. Reagent information can include the type of reagents in a device, lot specific information, such as calibration information and expiration dating. Once a sample is correctly labeled, there is no longer a need for manual user intervention to enter this information. In fully automated embodiments, this information is stored along with test results and other pertinent information to create and maintain an accurate record of the tests and test results. As such, the chance for operator error in incorrectly identifying a sample or otherwise incorrectly entering information regarding a test, is minimized. Additionally, test results and other data relating to the test can be automatically stored along with the patient identification and other associated information such that data for a patient can easily be accessed.

Another embodiment of the invention is to utilize an encoder, such as for example a magnetic strip encoder, in the instrument to encode information on an assay device. For example, patient information, including patient number, tests to be performed and the like can be entered through the keypad of the instrument or via a centralized computer that downloads the information to the fluorometer. The encoder records the information onto the assay device, such that when the user inserts the assay device into the fluorometer, a reader reads the information on the assay device and combines the assay results with the encoded information. The combined information can be stored in the fluorometer and it can be communicated to a network for real time or later analysis.

Yet another feature of the invention is that internal data storage can be provided so that patient information and test results can be tracked in the form of a history log. For example, in a portable hand-held environment, a user or technician may test several samples of blood in a given time interval. The test results, along with the identification of the patient, can be stored in the local database such that a history log of tests and test results are maintained. This history log can then be downloaded via the communications interface or onto a removable media.

Still another feature of the invention is that in remote or in-home applications, the identification of the patient can be based on an automatic number identification (referred to as ANI). In this embodiment, when the patient's fluorometer dials the remote health care facility via a telephone network, the ANI signal provided by the telephone network is used by the health-care facility to identify the patient from which the communication originated. The ANI can be used in place of the an identification of the patient based on the encoded label, or in addition thereto to provide a cross check against potential identification errors.

Further features and advantages of the invention as well as the structure and operation of various embodiments thereof are described in detail below with reference to the accompanying drawings.

BRIEF DESCRIPTION OF THE DRAWINGS

FIG. 12, which comprises

DETAILED DESCRIPTION OF THE INVENTION

Figure 1:
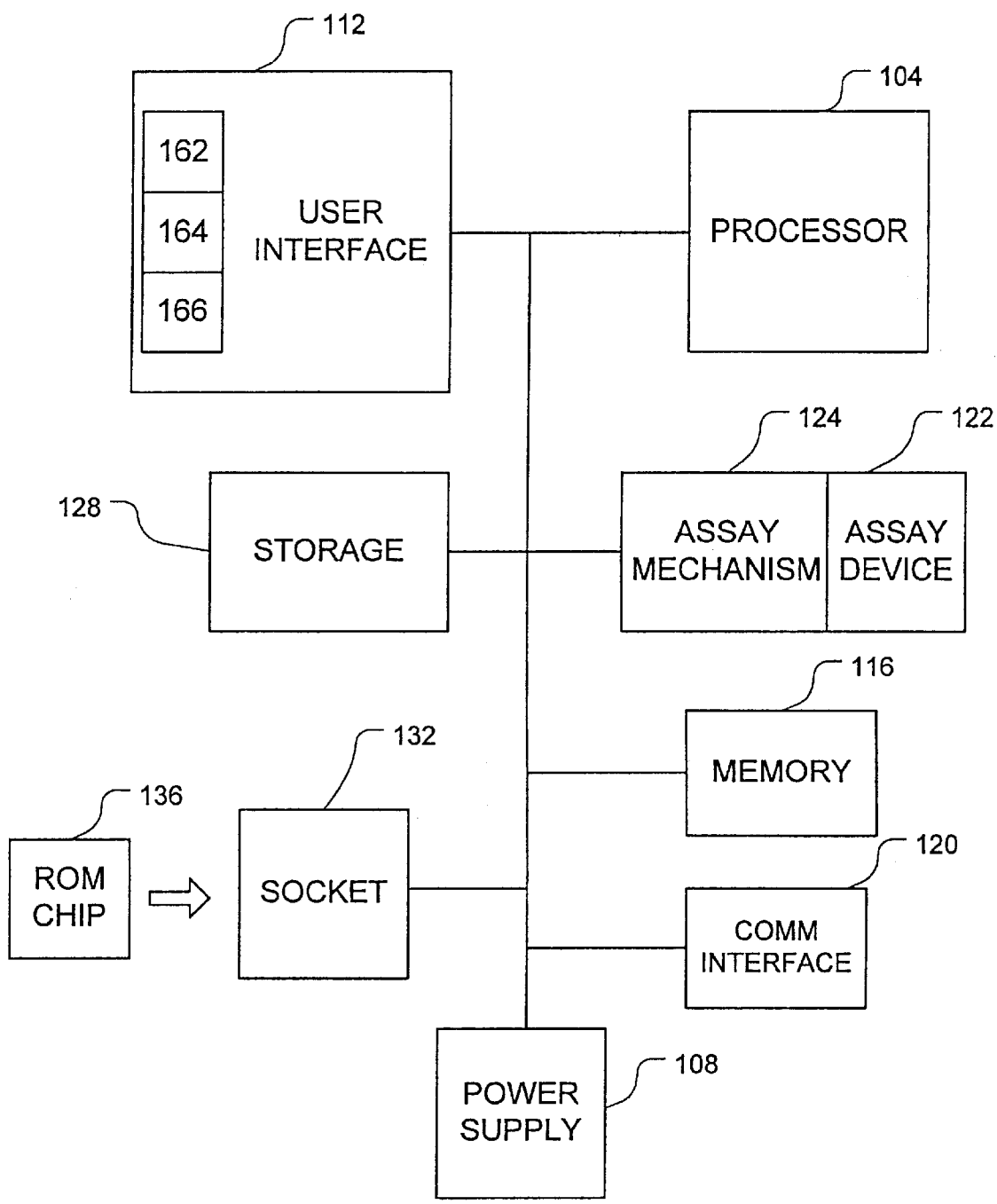
FIG. 1 is a diagram illustrating a representative functional architecture of a fluorometer according to one embodiment of the invention.

The present invention is directed to a system and method for performing fluorescent measurements including enhanced functionality. FIG. 1 is a diagram illustrating a functional block diagram of an enhanced fluorometer according to one embodiment of the invention. FIG. 1 illustrates examples of the functionalities that can be included with the automated fluorometer in terms of one example physical architecture, a central bus structure. After reading this description, it will become apparent to one of ordinary skill in the art how to implement any or all of the described functionality using one or more alternative architectures.

The enhanced fluorometer according to the embodiment illustrated in FIG. 1 includes a processor 104, a power supply 108, a user interface 112, a memory 116, a communications interface 120, an assay device 124, a storage device 128, and removable storage media. In the example illustrated in FIG. 1, the removable media include a ROM chip 136 and ROM chip socket 132, and a disk drive 138. Any or all of these functionalities can be included with an enhanced fluorometer depending on the particular application.

Processor 104 controls the operation of the fluorometer and also provides control for the various functionalities provided with the fluorometer. Processor 104 can be a central processor that controls the functionality via a bus structure or other communications interface. Alternatively, for example, processor 104 can be implemented by distributing the processing functions among one or more of the various components utilized to implement the functionalities of the fluorometer.

Power supply 108 is used to provide necessary power to the fluorometer and its components. Power supply 108 can be implemented using batteries, solar cells, transformers used to convert an AC power source, or other techniques to provide the appropriate power levels to the components. In one embodiment, power supply 108 is implemented using rechargeable batteries such as, for example, NiCad or Nickel Metal Hydride batteries which can be recharged using a charger connected to AC power from a conventional wall outlet. The use of rechargeable batteries provides a practical power source for portable applications.

User interface 112 provides one or more devices through which a user can interface with a fluorometer. In one embodiment, user interface 112 includes a keypad 162, a display 164, and a printer 166. Additional or alternative interfaces can be provided such as, for example, a keyboard, mouse, track ball, touch-screen display, or other user interface devices.

In one embodiment, keypad 162 is a small alphanumeric keypad that provides the user with input keys to assist in the direction of the functionality of the fluorometer. Keypad 162 can also include special function keys to perform single-touch operations. The function keys can be preprogrammed to perform specified functions, or user programs, depending on the application. Display 164 can be implemented using a number of display devices such as, for example, a small monochromatic LCD display. A small LCD display is preferable for portable applications because of its legibility and low power requirements. For non-portable applications display 164 can be implemented using, for example, a CRT or a color LCD display.

Likewise, printer 166 can be implemented using a variety of different printing techniques. For example, in the portable embodiment, printer 166 can be implemented using a small thermal printer such as that found on small calculators or adding machines. For non-portable applications, or applications where a portable fluorometer can be disconnected from the printer for mobility, larger printers can be used.

Memory 116 is used to provide storage for program data or other data used by processor 104 during operation. Memory 116 can be implemented using various RAM or ROM memory devices. Memory 116 can be used for example, to store operating instructions and to provide memory registers for operating and storage. Memory can also be used in conjunction with a storage device 128 such as a disk storage device. Storage device 128 can also be used to store program instructions, control and calibration curves, operational data, history logs, and other data which may be desired to be stored within the fluorometer. Preferably, storage device 128 is used to store large amounts of data, and the generally more costly but faster memory 116 is used to store only data which must be accessed more frequently or more rapidly. A cache can be provided to minimize latencies associated with retrieving frequently used data from storage device 128.

ROM chip socket 132 can be included to provide a means by which a ROM chip 136 containing program instructions, calibration curves, control data, or other information can be interfaced to the fluorometer.

Communications interface 120 can be provided to allow the fluorometer to communicate with various external devices. Depending on the desired applications and the environments in which the fluorometer is operating, various alternative communications interfaces can be provided. Communications interface 120 can be implemented to include wired and wireless interfaces such as, for example, an RS-232 interface, an infrared interface, an RF interface, a network interface, or other communications interface appropriate for the application. Through the use of communications interface 120, the fluorometer can share information with other entities such as test results, test statistics, and other information, as well as receive information and instructions from outside entities.

Assay mechanism 124 is used to perform the fluorometric readings on the sample in order to test the presence or concentration of one or more analytes. In one embodiment, assay mechanism 124 is a slide mechanism that is used to accept a small tray-like device, for example, an assay device. Assay mechanism 124 includes the optical components necessary to perform the fluorometric readings as well as a slide on which the assay device slides to position the assay zones in the appropriate location so that fluorescence can be measured in a reproducible manner. In one embodiment, the mechanism is motorized such that the assay device can be automatically loaded and ejected from the fluorometer as well as positioned with respect to the optics during testing. In this embodiment where the assay device is transported along a path in the slide, the path which includes optics used to excite the sample and sense the fluorescence. The path in which fluorescence is measured in the assay device is referred to as the diagnostic lane of the device.

In one embodiment, all of the data and instructions necessary to operate the fluorometer can be provided on ROM chip 136. In this embodiment, there is little or no need for functionalities provided by memory 116 and storage device 128. In other words, in one embodiment, all of the memory requirements of the fluorometer are provided by the ROM chip 136. In alternative embodiments memory requirements are shared among or redistributed to any or all of these storage devices.

In one embodiment, a removable storage medium, such as, for example, ROM chip 136 or a disk in disk drive 138 is utilized to provide operating instructions to the fluorometer. In a preferred embodiment, this memory device is a ROM chip 136. The functionality of the fluorometer is described in terms of this preferred embodiment. After reading this description, it will become apparent to one of ordinary skill in the art how to implement removable storage medium using other storage devices. In addition to operating instructions, ROM chip 136 can also be used to provide other pertinent data to the fluorometer to be used in controlling and calibrating the fluorometer as well as calibration curves for performing the various tests. In a preferred embodiment, ROM chip 136 includes test software used to conduct one or more tests. For example, test software can include program instructions used to direct the fluorometer to perform one or more fluorometric tests on a sample. Depending on memory space available on the ROM chip and test software size, one or more tests can be provided using a single ROM chip 136.

In one embodiment, each different type of test or assay is provided on a single ROM chip. In this embodiment, each time a different type of test is desired to be performed, ROM chip 136 is replaced with the appropriate ROM chip 136 containing the desired test software in socket 132. In a preferred embodiment, the test software and associated calibration and control information, and software for a plurality of tests can be provided on a single ROM chip 136. In this preferred embodiment, the need to exchange ROM chips 136 can be minimized. In a particularly preferred embodiment, the ROM chip 136 software is downloaded to the fluorometer so that a number of tests can be accessed by the fluorometer without changing ROM chip 136.

Where a plurality of tests can be provided on a single chip, user selection of those tests can be performed by user interface 112, or remotely via communications interface 120 or by bar code information on the assay device. An important functionality which can also be provided by ROM chip 136 is that different tests can be provided on different ROM chips such that "reprogramming" of the fluorometer to perform a variety of different tests can be accomplished simply by replacing ROM chip 136.

ROM chip 136 can also include calibration curves utilized to perform the desired test Because different tests typically utilize different calibration curves, in one embodiment, the calibration curves are provided on ROM chip 136 along with the test software. ROM chip 136 can also include control and calibration data to calibrate the fluorometer using controlled solutions. Because control and calibration information may change based on the test being performed, this information in one embodiment is provided with each ROM chip 136 such that the fluorometer can be properly configured and calibrated to perform the desired tests.

ROM chips 136 containing instrument specific, test specific, and calibration specific information can be the same or different. In a preferred embodiment, specific chips are used to provide specific functionality. Examples of this functionality are now described according to one embodiment of the invention. Instrument specific operational software for one or more tests resides on a single ROM chip 136 termed a program ROM key. A chip termed a reagent code chip provides test specific information, including calibration information for one or more tests and lots of tests. Control solution information, including concentrations and ranges of analytes and expiration dating of the solutions resides on another ROM chip 136 termed QC Sample Code Chip. Calibrator solution information, including concentrations and ranges of analytes and expiration dating of the calibrator solution resides on another ROM chip 136 termed Calibrator Code Chip. Information relating to the accessibility of a user to change fluorometer parameters, such as addition and deletion of user passwords, normal ranges for the analytes being measured, frequencies of measuring control solutions and the QC simulator, and the like on yet another ROM chip 13 termed Supervisor Code Chip. Additionally, information relating to expected values measured by a QC simulator resides on yet another ROM key 136 termed Instrument Validation Code Chip.

Figure 2:
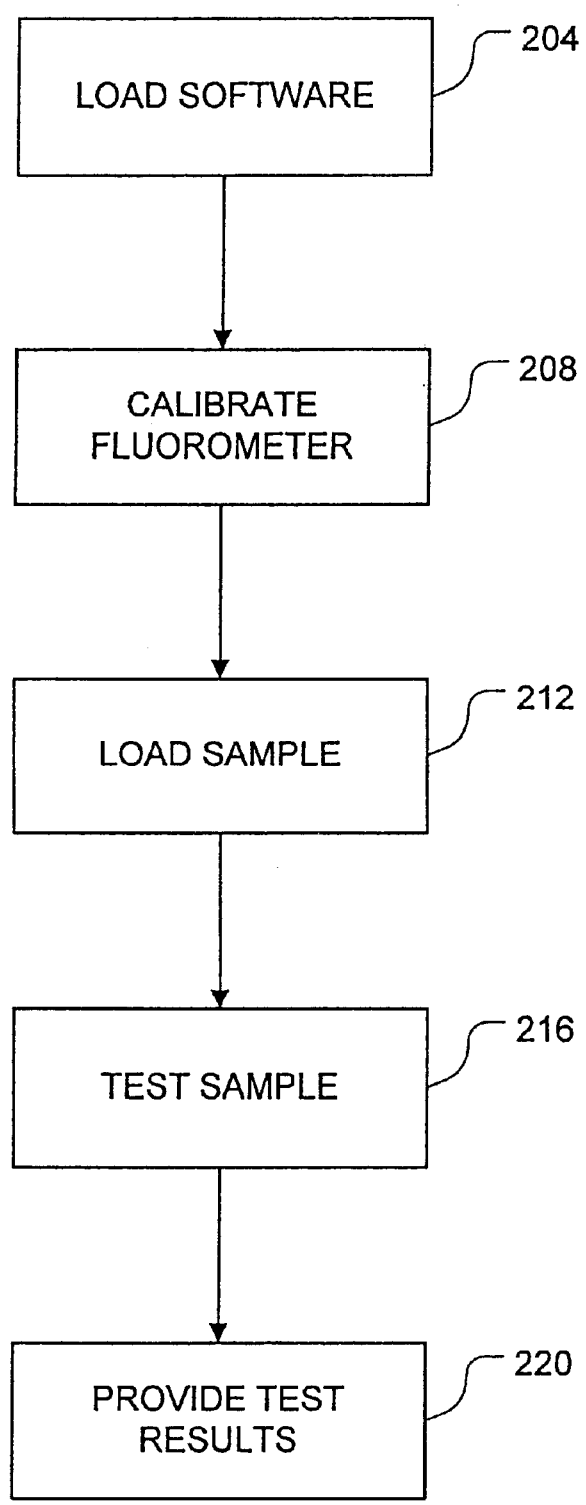
FIG. 2 is a diagram generally illustrating an operational scenario of the fluorometer according to one embodiment of the invention.

FIG. 2 is an operational flow diagram generally illustrating an operation of the fluorometer according to one embodiment of the invention. In a step 204 software is loaded to perform the desired test. In one embodiment, as described above, a ROM chip or memory device 136 is inserted into socket 132, the ROM chip 136 containing the software for the test to be performed. Alternatively, the test software can be loaded using communications interface 120, disk drive 138, ROM chip 136, storage device 128 or other interface. The loading can include the transfer of any or all instructions and data to internal memory 116 or storage 128, or can simply encompass making these instructions and data available to processor 104 via access of the utilized device or interface.

For a new type of test, or at periodic intervals during testing, it may be desirable to calibrate the fluorometer. As such, in a step 208, the fluorometer is calibrated. As disclosed above, the calibration can be performed using calibration software with controlled test solutions. In one embodiment, an assay device, termed a QC simulator, comprising a fluorescent zone or zones is inserted into the fluorometer. The fluorescent value of the QC simulator is a known value that can be loaded into the fluorometer via a ROM key or a bar code on the assay device. In another embodiment, a fluorescent chip, termed an internal calibrator, is within the fluorometer that is read by the fluorometer prior to each measurement of an assay device. The intensity of the fluorescence of the internal calibrator is a known quantity.

In a step 212, an assay device with sample to be tested is loaded into the fluorometer. In one embodiment, this is accomplished by inserting an assay device containing the sample into assay mechanism 124. In one embodiment, a bar code symbol or other encoded tag is used to provide an identification of the sample to be tested. In this embodiment, the encoded tag is read by the fluorometer such that the test results can be correlated with or later associated with the particular sample being tested. Examples of an encoded tag can include a bar code symbol, an encoded magnetic strip, a character designation capable of being read by an optical character reader, or a tag made using some other encoding technique.

In a step 216, the sample is tested. Samples to be tested can include, for example, biological fluid such as blood, serum, plasma, urine; a fecal extract and the like; an environmental sample such as water, a ground extract, a chemical and the like; or an extract of a food product. The testing is performed in accordance with the instructions provided by the software loaded in step 204. When an assay device is used as the carrier for the sample, various testing techniques can be used to optimize the test results. Examples of such techniques relating to immunological reactions are described in Principles and Practice of Immunoassay, C. P. Price and D. J. Newman, Macmillian Reference Ltd., 1997, and U.S. Pat. Nos. 5,028,535, 5,089,391, 5,143,852, 5,458, 852, 5,480,792 and 5,525,524 which are incorporated by reference herein. A preferred embodiment is used in conjunction with a motorized assay mechanism 124 to allow a plurality of sample zones or regions on an assay device to be tested.

In a step 220, the results of the tests are provided. The test results can be printed on printer 166, displayed on display 164, stored in a local memory or storage device within the fluorometer, written to a medium such as a disk in disk drive 138, or communicated to an external entity via communications interface 120. Preferably, the test results are displayed, printed, stored or transmitted along with the identification of the sample obtained using the encoded tag such that the test results can always be associated with the proper sample. The use of an encoded tag in this manner helps to assure that the test results are always associated with the proper sample.

Figure 3:
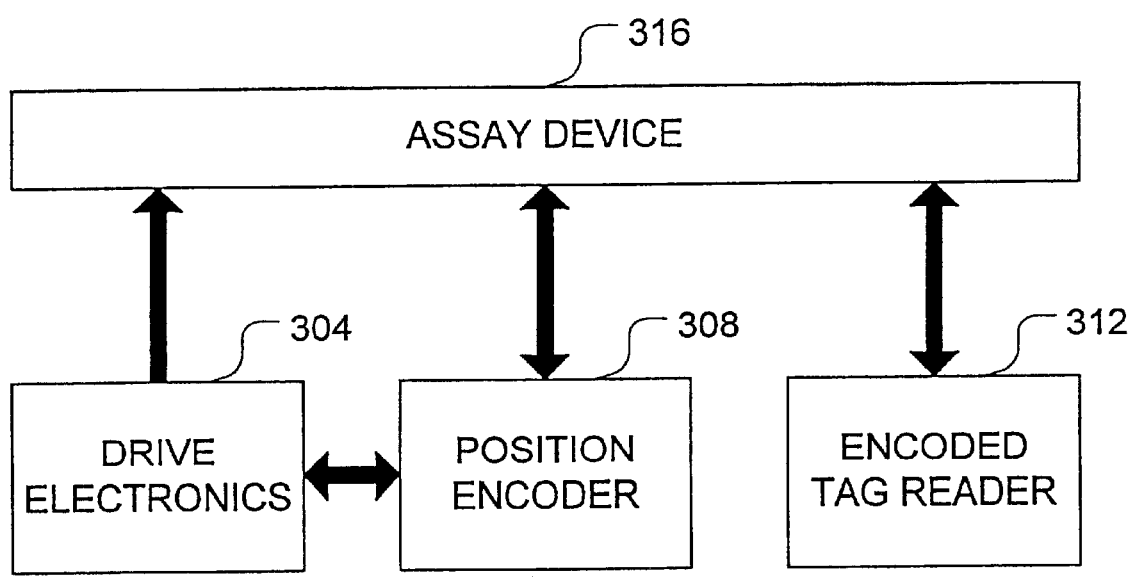
FIG. 3 is a diagram illustrating a representative functional architecture of the assay mechanism according to one embodiment of the invention.

FIG. 3 is a diagram illustrating an example implementation of an assay mechanism or assay device drive according to one embodiment of the invention. The assay device drive according to the embodiment illustrated includes drive electronics 304, a position encoder 308, and an encoded tag reader 312 such as, for example, a bar code reader. In one embodiment, drive electronics 304 includes a motor to position the assay device and a motor controller to control the motor. A friction drive, gear drive, or other mechanism can be used to translate the rotation of the motor into motion of the assay device. Drive electronics 304 are thus used to load and eject the assay device as well as to position the assay device with respect to the optics of the fluorometer, for example, along the diagnostic lane. In this embodiment, the assay device is moved in relation to stationary optics. In alternative embodiments, the optics can be moved instead of, or in addition to, the assay device.

Position encoder 308 is used to determine the position of the assay device within assay device drive 300. Position encoder 308 can obtain position information from the assay device itself such as, for example, by sensing an encoded label on the assay device. Alternatively, position encoder 308 can determine the position of the assay device based on the rotation of the drive shaft through the motor using well-known encoder techniques. Encoded device reader 312 is used to read the encoded tag provided on the assay device. In one embodiment, encoded tag reader 312 is a bar code reader that reads a bar code label on the assay device. Alternative embodiments can include, for example, a magnetic stripe reader, an inductive reader, or an optical character recognizer. An encoded tag reader 312 senses the encoded tag information from the label on the assay device and provides this information to processor 104. The encoded information can include information such as, for example, a patient I.D., an identification of the tests to be performed on the sample, an identification of the sample type, or other appropriate or pertinent information. This information can be used to log the test results as well as to control the type of testing performed or test parameters used.

In one embodiment, drive electronics 304 and position encoder 308 are used to control the positioning of the assay device, as well as to reposition the assay device during testing such that a plurality of regions of the assay device can be tested. This capability to position the assay device such that various portions of the sample can be tested allows enhanced testing algorithms to be utilized to produce improved test results. An example of enhanced testing routines that can be used where different regions of an assay device are tested is fully described in copending patent applications of common assignee, having application Ser. No. 08/311,098, and titled "Fluorescence Energy Transfer and Intramolecular Energy Transfer in Particles Using Novel Compounds" and application Ser. No. 08/409,298 also titled "Fluorescence Energy Transfer and Intramolecular Energy Transfer in Particles Using Novel Compounds," which are incorporated herein by reference.

Figure 4:
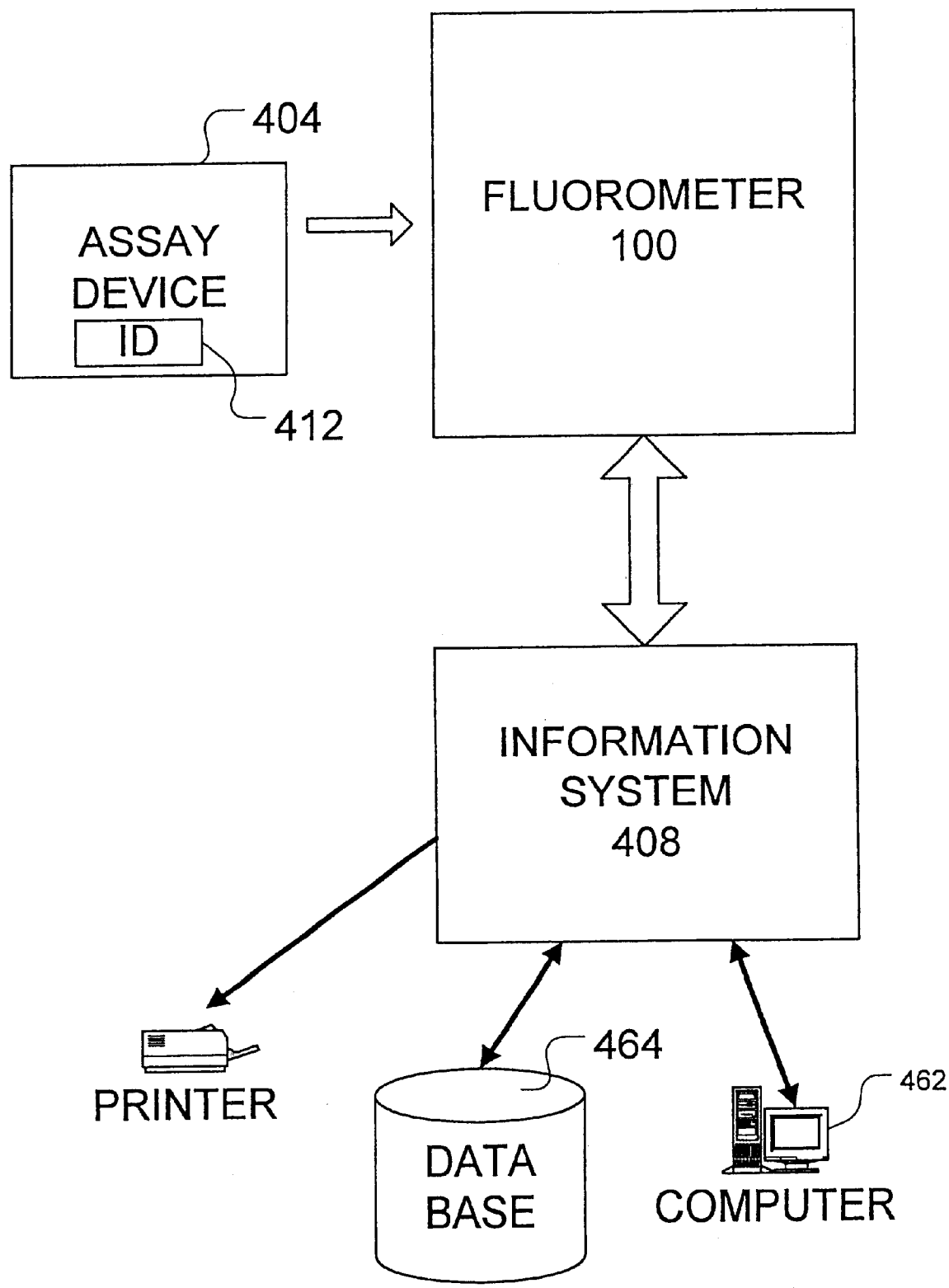
FIG. 4 is a diagram illustrating an example implementation of the fluorometer with a health care facility according to one embodiment of the invention.

FIG. 4 is a block diagram illustrating an example implementation of a fluorometer 100 used in communication with an information system 408 to perform fluorometric tests. As described above, a communications interface 120 can be provided to allow the fluorometer 100 to communicate with outside entities such as, for example, a hospital network, a physician's office, a testing clinic, other laboratory computers, or other relevant entities. To illustrate the utility of the communications interface, a simple example scenario is now described. In this example scenario, the outside entity is a health care information system 408 such as, for example, a hospital data system that can be accessed by a physician or other health care professional to order tests for and treat a patient.

In the example illustrated in FIG. 4, information system 408 is implemented to include a data entry terminal 462 and a data storage device 464. After reading this description, it will be apparent to one skilled in the art how information system 408 can be implemented using alternative architectures. In one example scenario, a blood sample is drawn from the patient. The vials containing the blood are labeled with an identification of the patient and sent to the lab that will perform the fluorometric tests. The technician at the lab receives the blood sample, prepares the assay device and places the encoded I.D. label 412 onto the assay device. I.D. label 412 identifies the assay device as belonging to the patient from which the sample was withdrawn. I.D. label 412 can be generated by the lab technician or transferred from the received vials.

Figure 5:
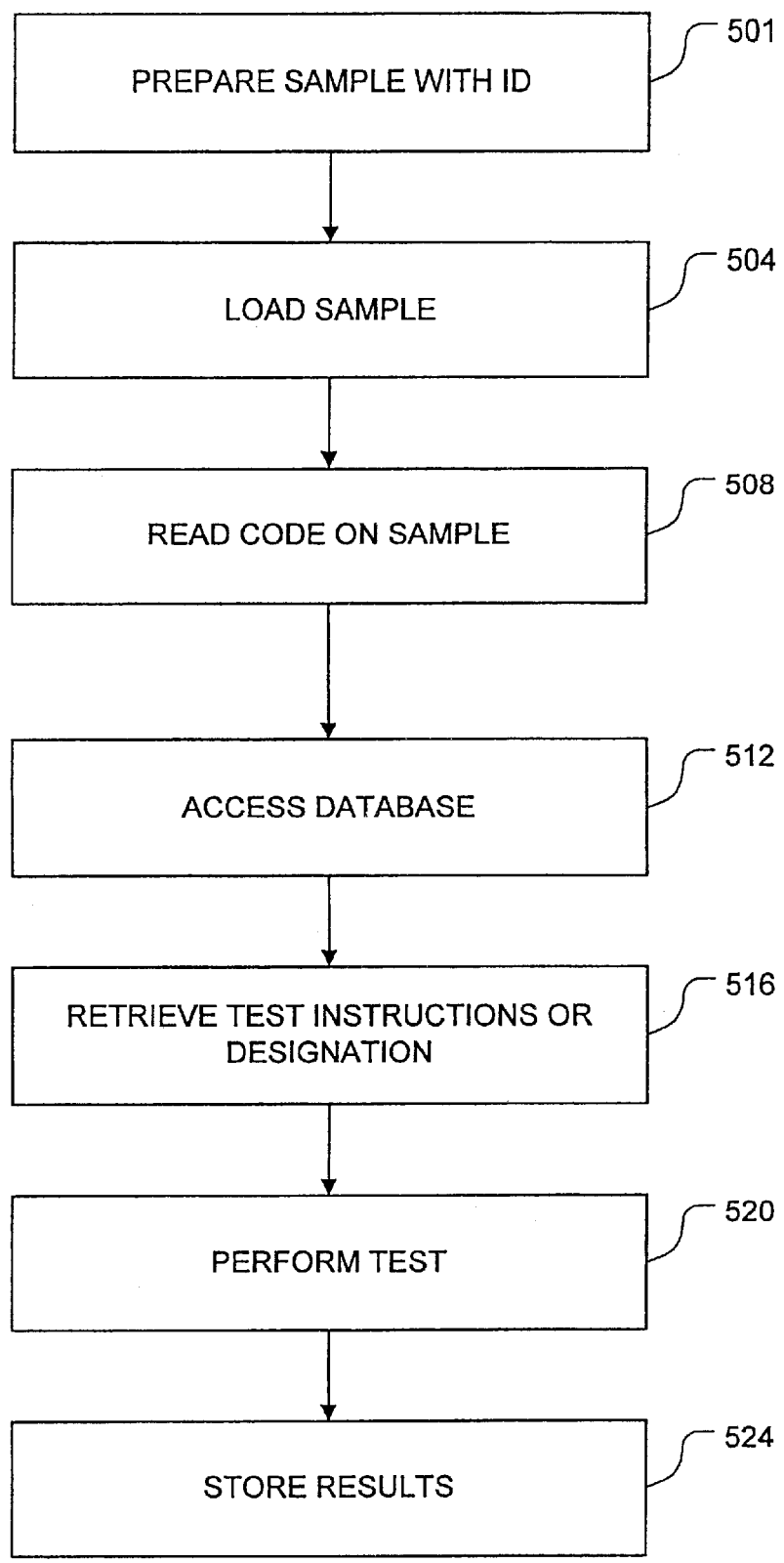
FIG. 5 is a diagram illustrating an operational scenario of the fluorometer in conjunction with a health care facility according to one embodiment of the invention.

FIG. 5 is an operational flow diagram illustrating an example process by which the sample can be tested in an automated fashion with fluorometer 100 in communication with information system 408 utilizing communications interface 120. In a step 502, an assay device is prepared with a sample and labeled with an encoded tag. In a step 504, the prepared sample, that is, an assay device with the sample added, is loaded into fluorometer 100. In one embodiment, the assay device is a cassette or tray-like container. The assay device includes an encoded I.D. tag 412 which can provide, for example, an identification of the patient from which the sample is drawn, an indication of the assay or assays to be performed and can include additional information as may be deemed relevant for the particular application. Any additional information required can be downloaded or entered by the health care professional via user interface 112.

In a preferred embodiment, the encoded I.D. tag 412 provides an identification of the type of test that is being performed, for example, a test that assesses the condition of a patient with respect to a myocardial infarction. In this preferred embodiment, the lab technician enters the patient information, for example, the patient number, via keypad 162. In yet another embodiment, an encoded label is not used and all necessary information is obtained through downloading, manual entry or a combination thereof.

In a step 508, fluorometer 100 reads the encoded tag on the assay device. In a step 512, information from encoded tag 412, and/or any additional information downloaded and/or entered, or a translation thereof, is sent to information system 408 to access information or to download information about the patient or about tests ordered for that patient.

For example, the health care professional at the hospital ordering tests for the patient can enter in the patient's name or other identification as well as a list or identification of tests ordered for that patient into system 408. The patient's name or identification and the tests to be performed for that patient are stored in database 464 so that there is a record of the tests ordered for that patient. Thus, in step 512, the information sent to information system 408 is used to access the database, to thereby retrieve information indicating which tests are ordered for the patient. In a step 516 test instructions which can include, for example, instructions for performing a desired test, or an identification of the test or tests ordered for the patient, are downloaded to fluorometer 100 using communications interface 120.

In a step 520, fluorometer 100 performs the test, after the technician loads the assay device, by either carrying out the downloaded instructions, or by accessing the instructions locally (e.g., by local storage, by input from keypad 162 or from ROM chip) based on an identification of the test received from information system 408. Where a different ROM chip 136 or disk needs to be installed to perform the required test, the user is informed via user interface 112.

In a preferred embodiment, the testing is performed automatically without user intervention. Indeed, in one embodiment, timing algorithms such as those described below are implemented to control the timing of the assay process. In this embodiment, the test is carried out and completed automatically without intervention. Alternative embodiments may provide the capability of the system to prompt the user for certain inputs as deemed appropriate.

Once the tests are completed, in a step 524, the results are provided to information system 408. The results can be stored in database 464 and are identified as being associated with the patient. As such, results of the tests can be accessed by health care professionals using terminal 462 and can be printed to provide a hard copy of the results.

Additional information regarding tests conducted on the sample can be transmitted to information system 408 as well. The additional test information can include, for example, an identification of the patient and other patient information, a sample identification, an identification of a test or tests performed on the sample, a date and time at which the tests were conducted, test conditions, test results and other pertinent information. This test information can be used to update database 464 such that information system 408 has a complete record of tests, results and associated data for a patient. Additionally, the test information can be stored in the fluorometer in local storage 128, memory 116 or on removable storage medium (i.e., ROM chip 136, removable disk, etc.).

In order to assure that all required tests are performed, and also to avoid duplication of testing, record flags or other techniques can be used when the database 464 is accessed to retrieve test instructions. For example, when fluorometer 100 accesses information system 408 to receive instructions for a particular test, that test is flagged as being performed such that subsequent accesses by this or another fluorometer 100 will not retrieve the same test instructions. Once a test is completed and the results provided to information system 408, another flag can be set indicating the status of the test as being completed.

Note that where tests are ordered which depend on the type of sample being tested, I.D. 412 can also include a sample identification or a sample type identification. For example, where a prepared sample is plasma, an indication of such is included on I.D. 412, or alternatively entered by the user using the keypad or other input device on fluorometer 100. Thus, when fluorometer 100 queries information system 408 to access test instructions, tests which are ordered for plasma are checked, and if present, retrieved from database 464. As illustrated by this example scenario, the chance for operator error in identification of the sample and performing the appropriate tests on that sample, are minimized at the fluorometer. In this scenario, once the sample is loaded with the correct I.D., tests ordered by the physician or health care professional at the hospital are electronically retrieved, automatically performed, and electronically reported back to information system 408. As such, there is little or no need for human intervention in this system, with the exception of addition of the sample to the assay device and insertion into the fluorometer by the technician.

In yet another example embodiment, label 412 can be used to further automate the testing process, even in a stand-alone environment. For example, in one embodiment, when the technician prepares the blood sample, the label 412 code includes a description or indication of the test to be performed on that sample. When the fluorometer reads the test description or indication, the appropriate test is performed. As with the remote example described above, the test can be automatically accessed from local storage or the user may be prompted to load the test-related information via ROM chip 136, disk or other memory or storage device. Information from the tag 412 as well as tests performed and their results can be used to create a record locally on fixed or removable media as well as remotely via communications interface 120. Information from the record can be used for patient diagnosis, accounting, billing, statistical and other purposes.

As would be apparent to one of ordinary skill in the art after reading the above descriptions, there are numerous scenarios that can be implemented to take advantage of the capabilities of fluorometer 100 utilizing an encoded I.D. label 412 and communications interface 120. Also, as described above, communications interface can take on a variety of different physical embodiments such that communication between fluorometer 100 and information system 408 can be implemented using a wireless communication link, a hardware communication link, networks communication, or other communication facilities.

As an example alternative application to that described above with reference to FIGS. 4 and 5, consider an application in which a patient utilizes fluorometer 100 to conduct in home testing. In this application, the patient obtains a sample and places it in the assay device or cassette. The sample can be a blood sample, for example, from a finger prick, a urine sample or other appropriate sample.

Fluorometer 100 can be pre-loaded with test instructions appropriate to the particular patient. Alternatively, fluorometer 100 can utilize communication interface 120 to access test instructions from the clinic, physician's office, hospital or other health-care facility. The patient loads the sample into fluorometer 100 and the appropriate test or tests are conducted.

Test results are forwarded to the health care facility using communications interface 120 so that the patient's records can be updated and the appropriate health care professional can be apprised of the results.

Fluorometer 100 can include an alarm feature that automatically informs or reminds the patient when a test is required. This feature can be implemented, for example, using a built-in programmable clock. The clock can be programmed manually or by installing scheduling instructions. For example, a scheduling program detailing the type or types of tests to be performed and the time for such tests can be installed before fluorometer 100 is delivered to the patient. The installation can be performed, for example, using removable storage media. Schedule programming can also be downloaded via communications interface 120 both initially, and as treatment progresses. For example, the tending physician may wish to update the testing schedule by adding new tests, changing the testing interval, or discontinuing certain tests. The physician can update information system 408 to reflect this change and the changes can be downloaded via communications interface 120. In this manner, the testing can be tailored and updated to suit a patient's current needs.

In one embodiment, the scheduling program indicates the type of test to be performed at a scheduled test occurrence. Information regarding the test type can be, but does not need to be provided to the patient. This information, however, along with test results, is preferably provided via communications interface 120 to update the patient's data base or to inform the physician of the test results. The scheduling program can also indicate the sample type required for a particular test.

In embodiments where the communications interface is a telephone, the patient's identification can be provided to the health-care facility using automatic number identification, or ANI, based on the telephone number from which the test instrument is calling. Where ANI is not available, or where the patient is calling from a location where his or her ANI is not recognized, the system may prompt the patient to enter an identification.

In yet another embodiment, communications interface 120 can be utilized to inform the patient that a personal visit to the health-care professional is required. For example, consider a scenario in which the tending physician is obtaining and reviewing results of regularly conducted tests. The physician may detect a change in condition that warrants a personal appointment. The physician can input this information into the health care information system and the patient is appraised of the necessary appointment.

In one embodiment, the health care information system maintains a calendar of available appointment slots for the tending physician. The appointments can be maintained on the physician's personal computer or on a data server or other accessible data base within the health care information system to facilitate sharing of calendar information among health care professionals.

A listing of available appointments is sent to the patient via communications interface 120. The patient, using user interface 112 reviews the available appointment slots and selects one that fits his or her schedule. Fluorometer 100 provides this information to health care information system to reserve that slot for the patient. A reminder for the appointment can be programmed into the internal clock of fluorometer 100 to remind the patient a desired time interval before the appointment. Alternatively, the health care information system can store this information and send an appropriate reminder to the patient via communications interface 120.

The use of communications interface 120 in the in-home embodiments allows real-time or near-real-time interaction between the patient and the tending health-care professional although the patient and health care professional are not at the same location. Tests can be conducted and the results reported and analyzed as they are performed. Test schedules can be updated and otherwise modified as the health-care professional deems fit based on results of recent tests.

Figure 6:
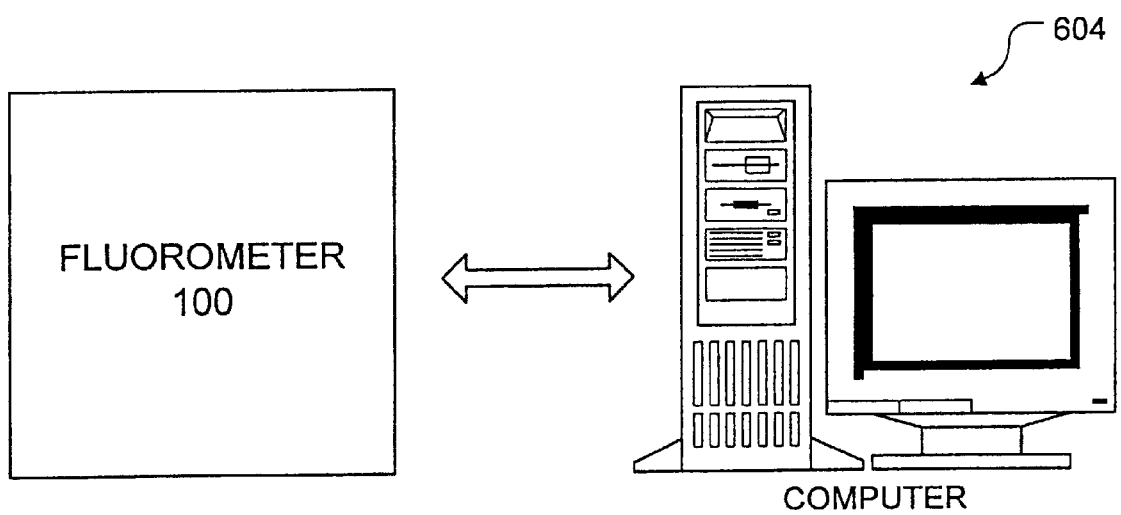
FIG. 6 is a diagram illustrating an example implementation of the fluorometer in conjunction with a separate computer according to one embodiment of the invention.

As described above, the fluorometer can be utilized in conjunction with a separate processor such as, for example, a workstation or personal computer. In this embodiment, a variety of fluorometer functionalities can be delegated to or shared with the separate processor. To further illustrate this capability, it is now described in terms of an example scenario. In this example scenario, fluorometer 100 is interfaced to a personal computer 604 as illustrated in FIG. 6. In one embodiment, the interface is implemented using an RS-232 communications interface, although other communications interfaces can be selected based on speed, cost and reliability tradeoffs.

As an example of the manner in which a processor such as a personal computer 604 can be utilized to enhance the performance of fluorometer 100, consider a scenario where fluorometer 100 performs a plurality of tests on blood samples. After performing the appropriate measurements and readings, the fluorometer provides these results to personal computer 604. In a sense, fluorometer 100 can be considered as providing raw data to personal computer 604 although a certain amount of processing can be performed by fluorometer 100. Personal computer 604 accepts the raw data and performs analysis and processing of the data to help to arrive at definitive test results or to interpret therapy for the patient based on the test results. Test results and related data can be described alphanumerically and graphically on the display screen of personal computer 604. Through user interfaces on personal computer 604 an operator can adjust the functionality of the test as well as test parameters to obtain optimum results.

Figure 7:
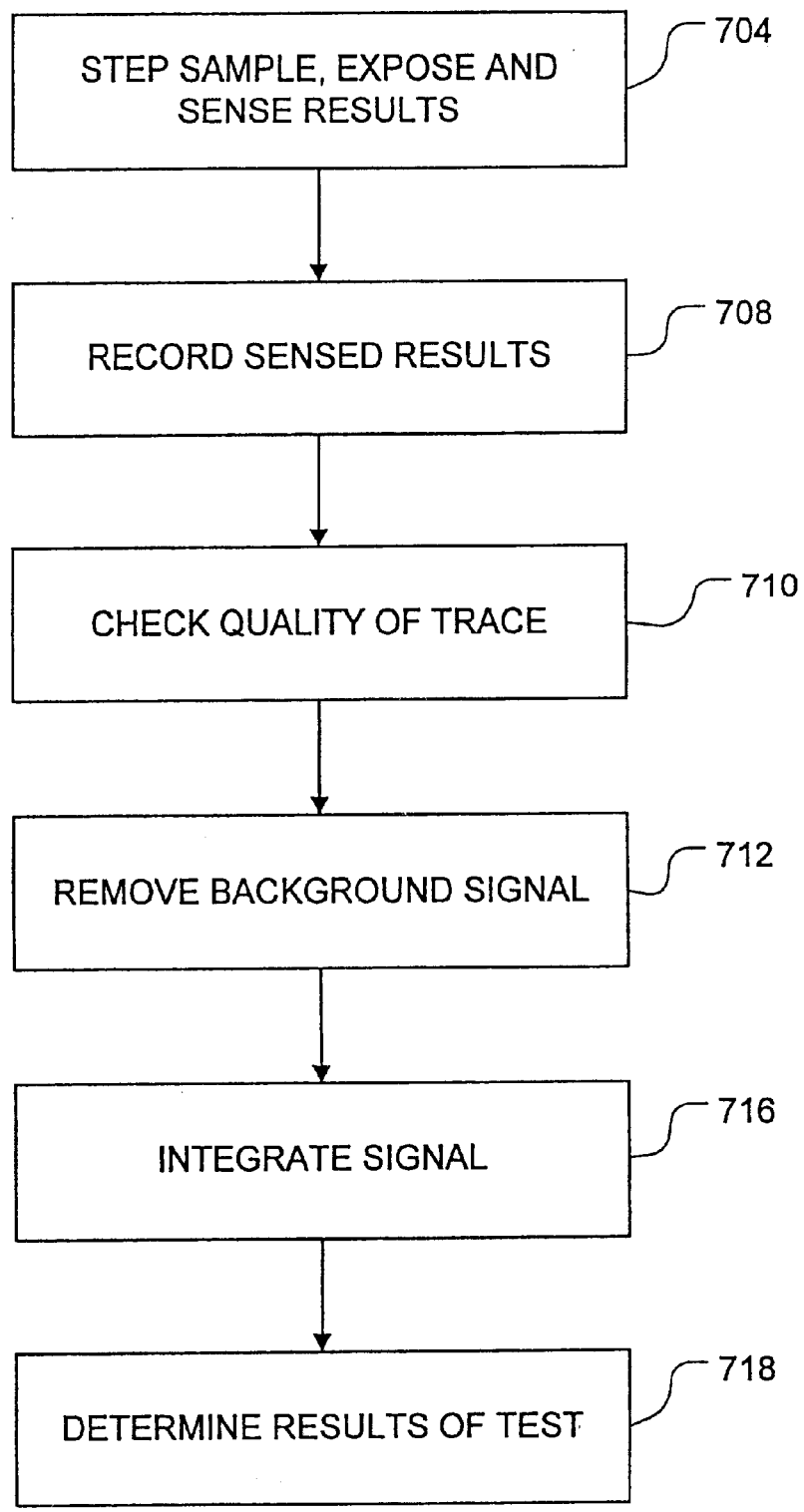
FIG. 7 is a diagram illustrating a process for testing a plurality of sample areas according to one embodiment of the invention.

As disclosed above, in one embodiment the assay device is repositioned during testing such that different areas of the sample can be excited and the fluorescence of each of these areas can be measured. An example process by which this is accomplished and the data analyzed now follows. FIG. 7 is an operational flow diagram illustrating this process according to one embodiment of the invention. In a step 704, the assay device is stepped along the diagnostic lane such that at each step a different region of the assay device is excited and fluorescent measurements are sensed from that region. In one embodiment, the assay device is stepped in only along one direction (e.g., back and forth or side-to side) and therefore the regions or zones are divided along one direction of the assay device. In alternative embodiments, the assay device can be stepped, for example, both back and forth, and side to side, such that additional regions on the assay device can be defined.

In a preferred embodiment, the assay device is stepped along the diagnostic lane in discrete steps, and fluorescence measured at each step. In alternative preferred embodiments, the assay device is driven continuously at a given speed along the diagnostic lane, and measurements are taken throughout the process. In either embodiment, the measurements themselves can be at discrete intervals or continuous.

In a step 708, the results of each region are recorded. In embodiments where the device has a fluorescent result, the recorded results represent optical amplitudes sensed from the excited region. Preferably, the data from a particular sample are recorded and processing is performed upon recorded data such that processing does not have to be performed in real time, and the entire data sample can be utilized in processing.

In a step 710, data processing begins with checking the quality of the trace. The details of this step according to one embodiment are fully described in copending patent applications of common assignee, having application Ser. No. 08/311,098, and titled "Fluorescence Energy Transfer and Intramolecular Energy Transfer in Particles Using Novel Compounds" and application Ser. No. 08/409,298 also titled "Fluorescence Energy Transfer and Intramolecular Energy Transfer in Particles Using Novel Compounds."

As the assay device is stepped along and moved in relation to the optics, nonspecific binding of the fluorescent label results in a residual fluorescent signal. This signal is a background signal that can be highly variable from sample to sample. Therefore, in a step 712 it is desired to remove this signal before calculating the amount of fluorescence immobilized on each area of the diagnostic lane for each sample tested. The fluorescence intensities measured for each area or region tested are integrated to determine the total amount of fluorescent label immobilized as a result, for example, of an immunological binding reaction.

In a step 716, the processed signal without the background is integrated to determine the total fluorescence of the sample. In a step 718 the result is computed, for example by comparison to a threshold, to determine whether the test is positive or the concentration of each analyte being tested.

In fluorometer embodiments, the sensed amount of fluorescent label is a function of the acquisition method. More specifically, the sensed amount of fluorescent label for a given region is the product of the fluorescent strength emitted by that region and the width of the region. Therefore, if the displacement of the assay device varies from the expected displacement the results obtained will be inconsistent and will not be reproducible. For example, if the displacement is shorter than expected, the amount of fluorescent label in the region will be reported as higher for a given sample.

To compensate for changes or inconsistencies in positioning, position encoder 308 can be utilized to obtain a measurement of the actual or relative displacement during the test process. In a preferred embodiment the position is encoded by monitoring the rotation of the motor, i.e. using a rotary position encoder. After reading this description, it will become apparent to one of ordinary skill in the art who to implement this functionality utilizing alternative embodiments of rotary encoders. From this, errors in the expected displacement arising from changes in motor speed are factored out.

However, imperfections in the drive mechanics and variations in the load on the drive mechanics can result in errors between the measured motor position and the actual assay device position. In a preferred embodiment the average error between the measured motor position and the assay device position is recorded as a function of the position of the assay device. This information is used to map the measured motor position into actual assay device position. In a particularly preferred embodiment the position is encoded by monitoring the position of the assay device with respect to the optics, i.e. using a linear position encoder. After reading this description, it will become apparent to one of ordinary skill in the art who to implement this functionality utilizing alternative embodiments of linear encoders. As a result of this process, inconsistencies in motion can be factored out to obtain a more accurate and reproducible test result.

Figure 8:
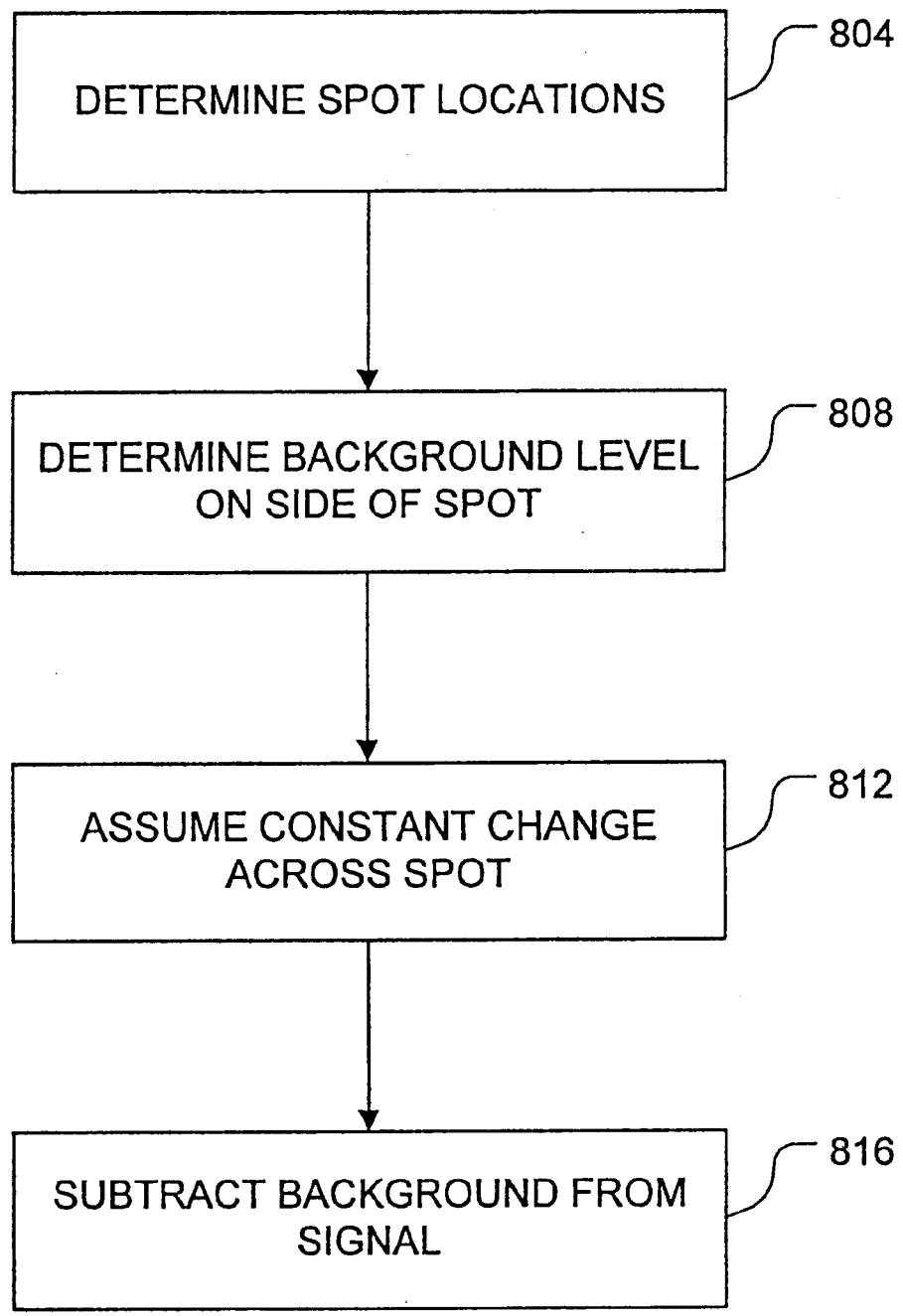
FIG. 8 is a diagram illustrating a process for removing a background signal from the test results according to one embodiment of the invention.

FIG. 8 is an operational flow diagram illustrating a manner in which the background signal can be removed according to one embodiment of the invention. In a step 804, the spot locations or zones of fluorescence as a result of the assay process are determined by where a signal is received. Alternatively, in a preferred embodiment, spot locations or assay zones are defined by the fluorometer software such that the fluorometer is programmed to measure fluorescence in a particular location or locations along the diagnostic lane of the assay device. These spot locations or zones are the points along the length of the diagnostic lane of the assay device at which an amplitude above a determined threshold is received.

Figure 9:
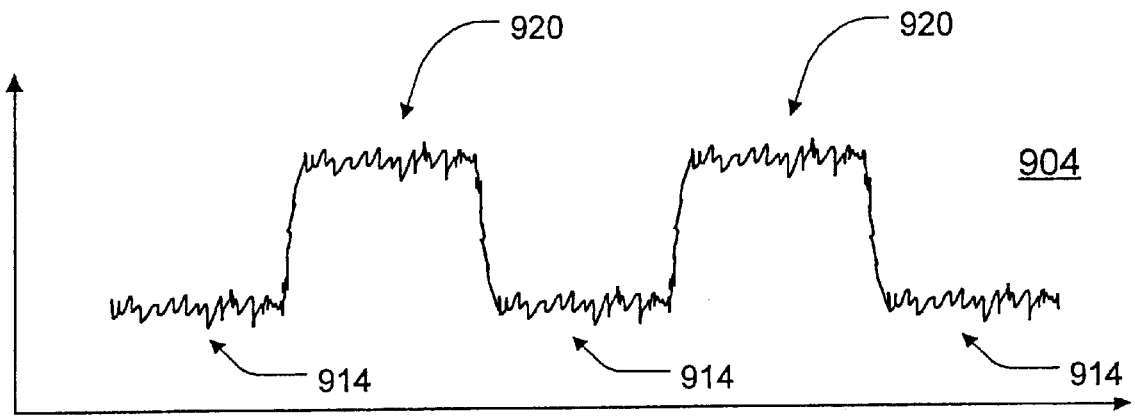
FIG. 9 is a diagram illustrating an example of spot locations in terms of signal strength according to one embodiment of the invention.

FIG. 9 is a diagram illustrating an example of spot locations along the length of the diagnostic lane. In FIG. 9, the ordinate is the amplitude of the fluorescent signal received, and the abscissa is the length along the diagnostic lane. Because the assay device is moving along the diagnostic lane, this also represents the position of the assay device with respect to the optics. Thus, travel along the abscissa represents a position in the diagnostic lane along the assay device. As illustrated in FIG. 9, there are areas where it is apparent that a signal is received as illustrated by spot 920, separated by areas in which there is merely background noise 914. Areas of apparent signal readings are referred to as spot locations or (assay) zones 920.

Figure 10:
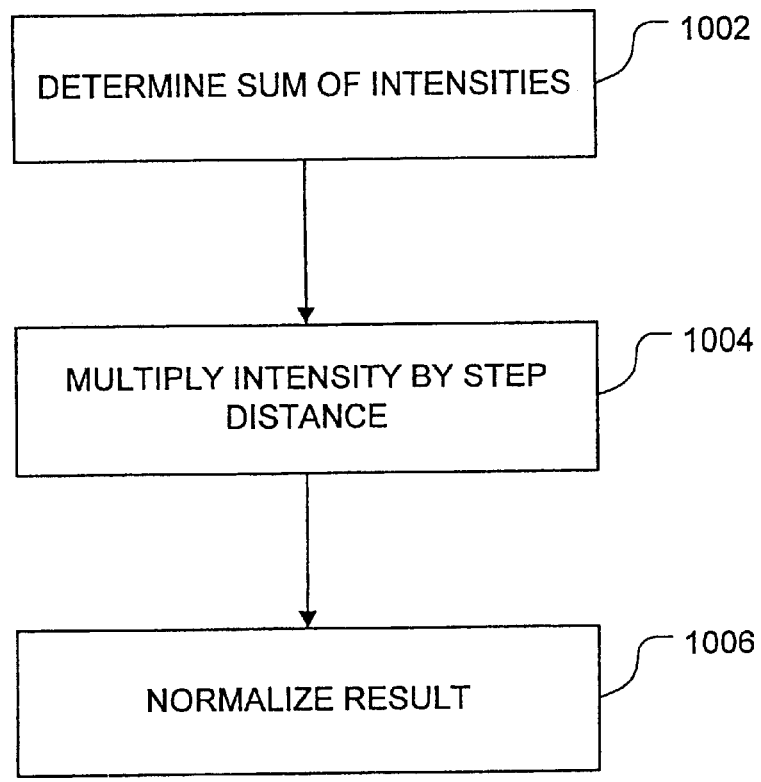
FIG. 10 is a diagram illustrating a process for integrating fluorescent intensity over the test range according to one embodiment of the invention.

In a step 808, the level of background signal 914 on either side of a spot 920 is determined. In a step 812, the level of background signal from one side of the spot to the other side is assumed to have a constant variation. This level is considered the background and is subtracted from the signal level of the spot location in a step 816. As a result of this process, a representation of the actual signal level without the contribution of the background noise can be determined. FIG. 10 is a diagram illustrating a process by which the fluorescence intensity is integrated over each spot 920 according to one embodiment of the invention. In a step 1002, the sum of the adjusted fluorescent intensity is calculated.

In a step 1004, this intensity is multiplied by the step distance between each point. The step distance relates to the amount by which the assay device is moved along the diagnostic lane between each data reading. In one embodiment, variations in the step distance are factored out of the readings in step 1004 by correcting the step distance according to previously measured calibration data.

In a step 1006, this result is normalized by the appropriate meter gain. The meter gain (G) is a scale factor that represents the relative intensity of the excitation source and the relative sensitivity of the detector. The detected signal is the product of the source intensity, the amount of fluorescence and the sensitivity of the detector. In one embodiment, the result is normalized by the width of the spot and therefore relates to the average amount of fluorescent label as a result of the assay process. In a preferred embodiment, the result is not normalized by the width of the spot and therefore relates to the total amount of fluorescent label as a result of the assay process.

The source is subject to both frequency and intensity drifts. These variations are tracked jointly with a fluorescent spot in the meter with known response at the nominal power and wavelength of the source. Therefore, the fluorescent signal of the test zone will scale proportionally to the variation in measured signal from the internal standard. One skilled in the art will recognize that the internal standard will correct any fluctuations in the sensitivity of the detector as well. In a preferred embodiment, step 1006 also normalizes the result to the measured signal of the internal standard.

In a preferred embodiment, the intensity ($I_j$) at each region is measured by subtracting the baseline signal (BL) from the measured signal (MI), $I_j=MI_j-BL_j$, as illustrated in FIG. 8. The intensity of each region is then multiplied by the length of each region, e.g. the known distance between measurements. The length of each region, $\Delta X_j$ can be a function of position along the diagnostic lane and is not necessarily a constant.

The sum of this product for each region within a zone represents the uncorrected fluorescent label (UFL) within the zone (UFL=$\Sigma I_j \Delta X_j$) The UFL is multiplied by the meter gain, which scales the result to be independent of the meter. The UFL is also multiplied by the expected internal standard value (EISV) and is divided by the measured internal standard value (MISV), yielding an instrument independent result of the total fluorescent label (TF).

Conventional fluorometers used to measure fluorescence of a sample typically operate in the visible or near-visible wavelength range. These assay methodologies utilize dyes that fluoresce, generally between 400 nm and 500 nm. Such dyes include but are not limited to fluorescein and methyl-umbelliferyl phosphate. However, blood, plasma and serum samples themselves absorb and fluoresce in the ultraviolet and visible spectrum, up to about 600 nm. As a result, the signal-to-background ratio of the signal sensed from the fluorescent dye is eliminated or diminished.

To overcome these difficulties, a preferred embodiment of the invention utilizes dyes that excite and emit in the infrared or near-infrared range, particularly between about 600 nm to 1300 nm. As a result of these characteristics, certain advantages can be gained. First, the excitation wavelength of the dye is not a wavelength that, for example, the blood or serum absorbs. As such, energy from the excitation source is not lost. Second, the emission wavelength does not correspond to the absorption of the sample such that fluorescent light is not lost. Finally, because the blood and serum do not fluoresce at these wavelengths, there is reduced background noise sensed by the detector.

Another preferred embodiment makes use of dyes that possess Stokes shifts greater than about 90 nm. Stokes shifts of greater than 90 nm allow simplification of the design of the optical block, in that special band pass filters are not necessary to block excitation light energy. In other words, the overlap of excitation and emission light is minimized as the Stokes shift increases, thus increasing the recovery of fluorescent light from assay device. One skilled in the art recognizes that the overlap of wavelengths of excitation and emission light requires the use of band pass filters to prevent measuring the excitation light when it is desirable to measure the emitted light. The use of band pass filters has the disadvantages of cost and of decreasing the yield of measured fluorescent light.

Dyes that exhibit properties of excitation and emission wavelengths in the near infrared and infrared and have Stokes shifts greater than about 90 nm are fully disclosed in copending U.S. patent application Ser. No. 08/601,492, titled "Fluorescence Energy Transfer in Particles," application Ser. No. 08/274,534, titled "Fluorescence Energy Transfer in Particles," application Ser. No. 08/311,098, titled "Fluorescence Energy Transfer and Intramolecular Energy Transfer in. Particles Using Novel Compounds," and application Ser. No. 08/409,298, titled "Fluorescence Energy Transfer and Intramolecular Energy Transfer in Particles Using Novel Compounds," which are incorporated herein by reference. A preferred embodiment utilizes dyes and dye systems of phthalocyanines and hybrid phthalocyanine derivatives that incorporate fluorescence energy transfer in particles, particularly in latex particles having bound antibodies, proteins, ligands and ligand analogues.

Figure 11:
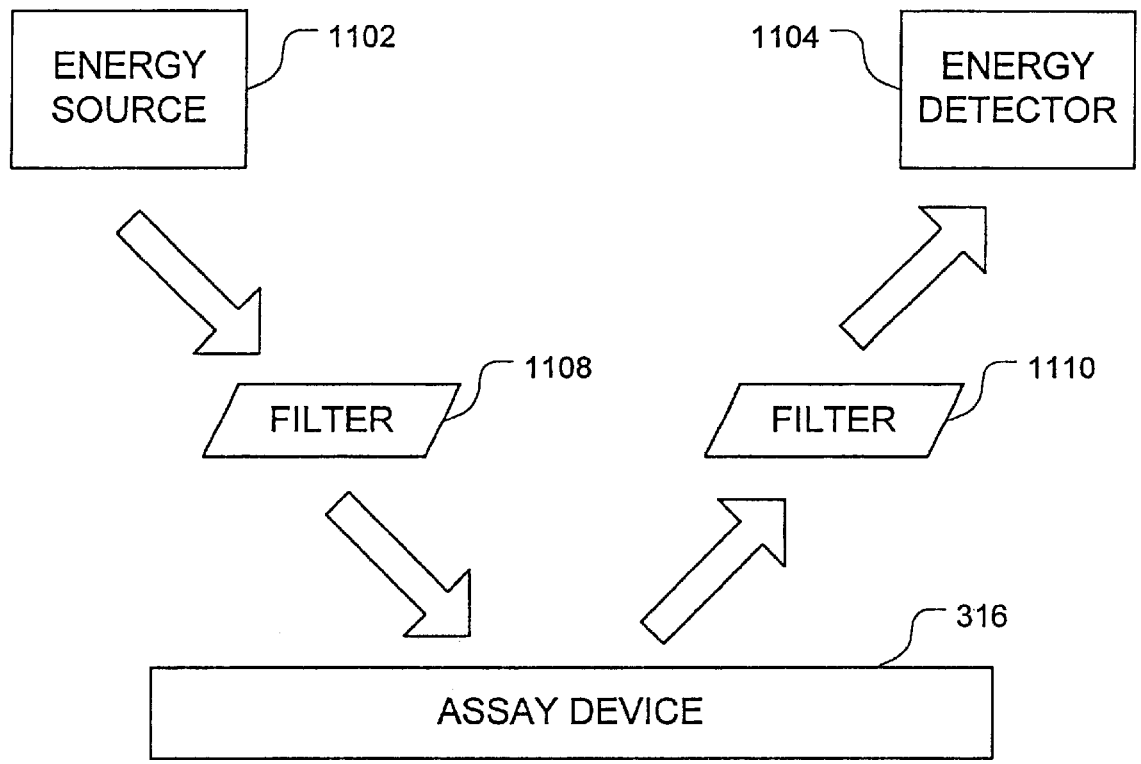
FIG. 11 is a diagram illustrating an optical package used to excite the sample and receive the signal according to one embodiment of the invention.

FIG. 11 is a block diagram illustrating an example implementation of an optical package that operates effectively with dyes exhibiting these desired properties according to one embodiment of the invention. The optical package illustrated in FIG. 11 includes an energy source 1102 and an energy detector 1104 (i.e., an optical transmitter and receiver). Additionally, cut-off or band-pass filters 1108, 1110 can be provided to filter background signal from the energy source 1102 or other sources.

Energy source 1102 is preferably an optical energy source 1102 that emits light in the infrared or near-infrared range portion of the spectrum, but can also emit light in the ultraviolet or visible wavelengths. In a preferred embodiment, optical energy source 1102 emits energy at a wavelength of approximately 670 nm. This wavelength of energy is poorly absorbed by blood or serum and does not cause blood or serum to fluoresce, at least not appreciably. Preferred energy sources are flash lamps, light emitting diodes and laser diodes. Particularly preferred energy sources are laser diodes.

Depending on the dye used, the fluorescent energy emitted from the sample is at a wavelength different from the excited energy. Specifically, in a preferred embodiment, the wavelength of the energy emitted as a result of the fluorescence of the dye is at approximately 760 nm. This wavelength is sufficiently different from that of the excitation wavelength (670 nm), such that energy (excitation) source 1102 will not significantly contribute to the background signal measured by the energy detector 1104. In a preferred embodiment, a cutoff filter is used to minimize light greater than about 690 nm from the source.

To further improve the signal-to-background ratio of the system, one or more filters can be included. In a preferred embodiment, for example, a high-pass filter 1108 is used to cutoff frequencies of the energy source at frequencies below (wavelengths above) the preferred excitation wavelength which would potentially be a source of background for energy detector 1104. Additionally or alternatively, a low-pass filter 1110 can be included to cutoff frequencies of the energy source at frequencies above (wavelengths below) the preferred detection frequency. Preferred energy detectors are photomultiplier tubes and silicon photodiodes. Particularly preferred energy detectors are silicon photodiodes.

In one embodiment, energy source 1102 and energy detector 1104 are positioned such that the excitation energy emitted from energy source 1102. impinges on the sample at approximately a 45 degree angle. Alternative configurations can be implemented using different angles. Additionally, a plurality of energy sources 1102 and/or detectors 1104 can be implemented to optimize the energy readings. One skilled in the art will recognize that sources generally do not provide uniform illumination, and furthermore, a 45 degree angle of incidence will result in a variation in illumination across the sample. In a preferred embodiment, source 1102 contains a special optic that provides for homogenous illumination of the sample. In a preferred embodiment this special optic is a micro-lens array. In a particularly preferred embodiment the special optic is a diffractive optic, which provides homogenous illumination, including correction for the 45 degree angle of incidence.

Because the output of light sources such as laser diodes often have non-uniformities, inconsistent results may be obtained from one light source to the next. To account for these non-uniformities a flattener can be used in one embodiment to achieve a more uniformly distributed beam pattern. Examples of such flatteners can include diffusers and diffractive optics.

As described above, a removable storage medium can be included to facilitate or enhance the operation of a fluorometer. Specifically, in one embodiment described above a removable storage medium is implemented using a socket 132 and a ROM chip 136. Preferably, in this embodiment, ROM chip 136 is mounted in a chip carrier that includes contacts to interface with socket 132. In this embodiment, the chip carrier can be inserted into and withdrawn from socket 132 to facilitate the change or swapping out of ROM chips 136. An example of ROM chip carrier is now described.

Figure 12A:
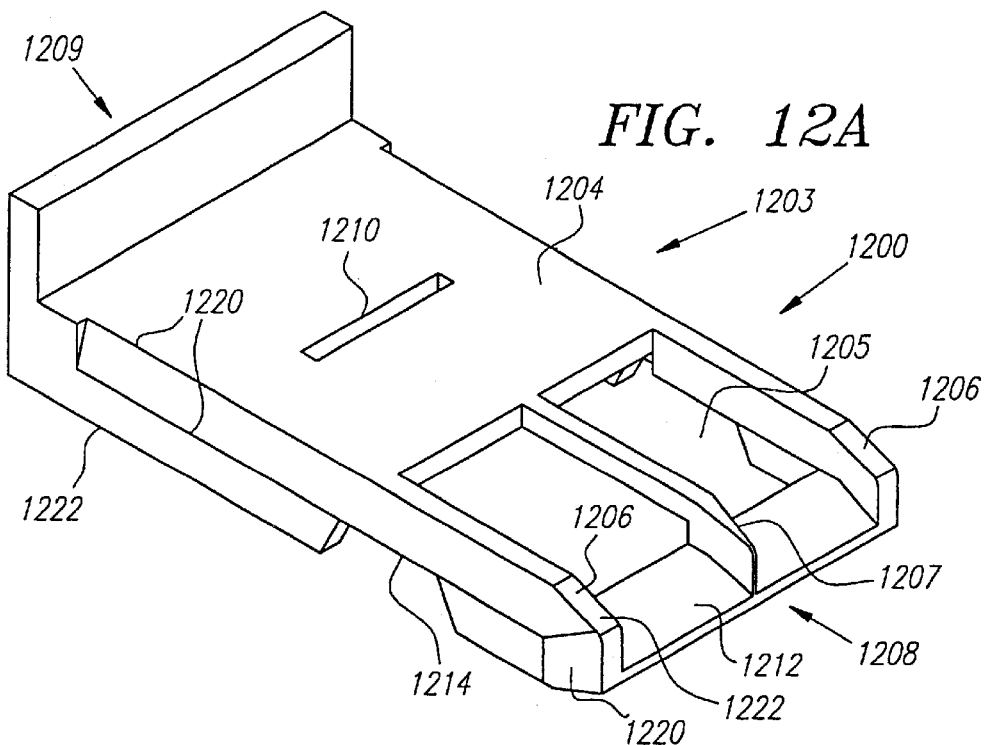
FIGS. 12A and 12B, is a diagram illustrating an example implementation of a chip carrier according to one embodiment of the invention.
Figure 12B:
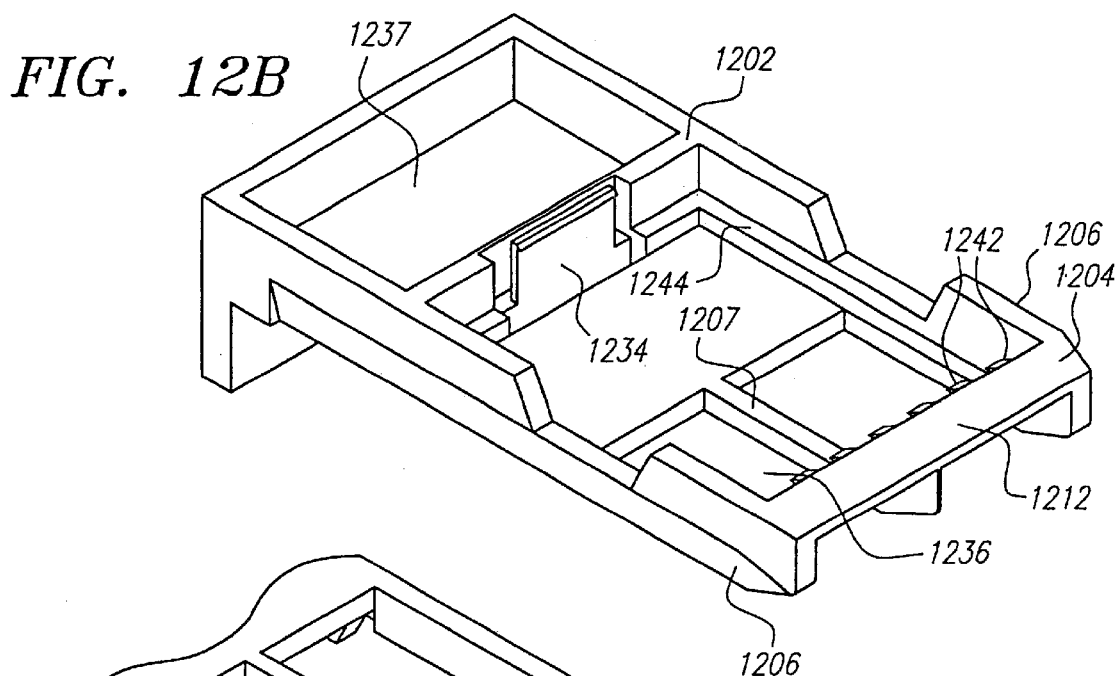

FIG. 12, which comprises FIGS. 12A and 12B, is a diagram illustrating an example implementation of a chip carrier 1200 according to one embodiment of the invention. FIG. 12A is a perspective view of what is referred to as the top surface of chip carrier 1200. As illustrated in FIG. 12A, chip carrier 1200 includes a body portion 1203 and a rear tab 1209. Body portion 1203 includes a structure for mounting a ROM chip 136, as well as for guiding ROM chip 136 into socket 1321 Rear tab 1209 provides a tab-like structure that facilitates the handling of carrier 1200 and the insertion and removal of carrier 1200 into and out of socket 132.

Figure 14:
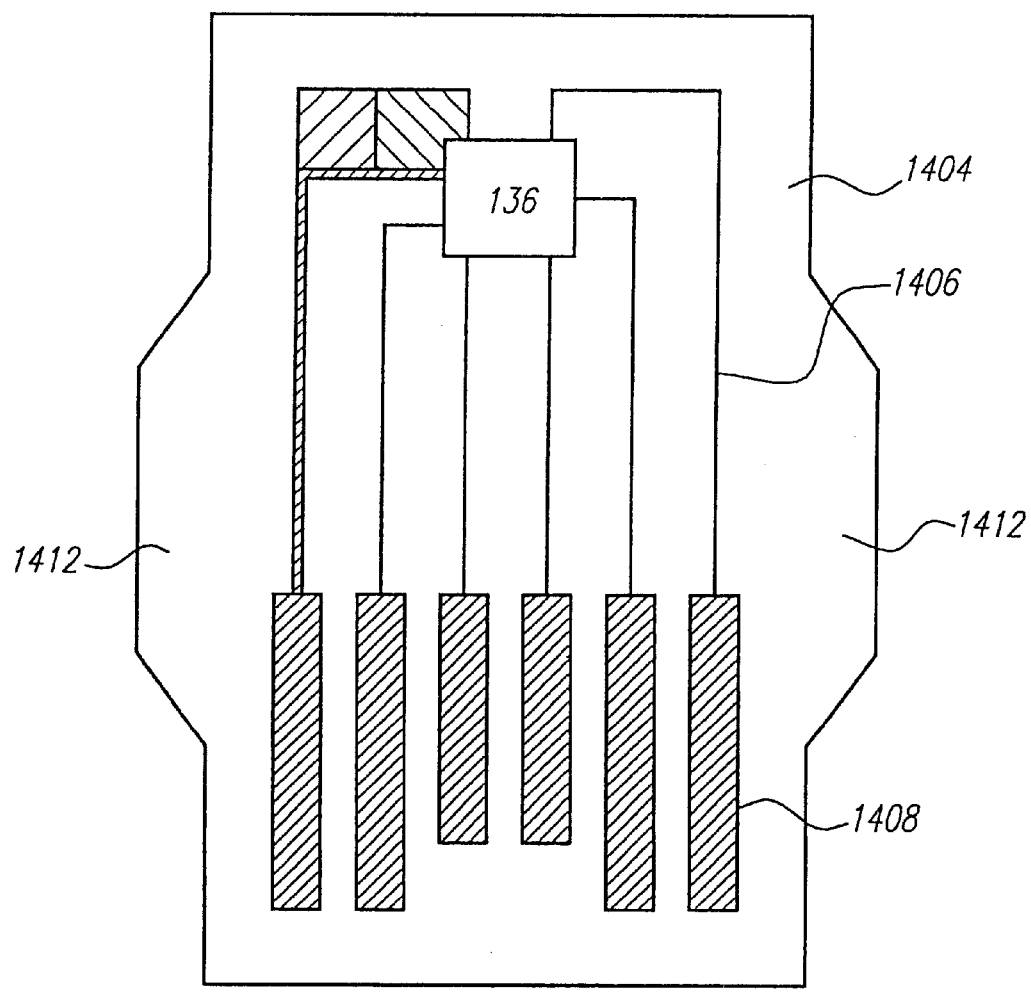
FIG. 14 is a diagram illustrating an example implementation of a ROM chip mounted on a printed circuit board according to one embodiment of the invention.

In the embodiment illustrated in FIG. 12, carrier 1200 includes a top face 1204 that has an open area 1205. Open area 1205 provides an opening through which contacts in socket 132 can access electrical contacts 1408 (illustrated in FIG. 14). Lateral members 1206 define the sides of carrier 1200 and form boundaries of open area 1205. A central member 1206 can be included to provide additional structural rigidity, as well as to assist in the guidance of carrier 1200 in socket 132. Leading edge 1208 of carrier 1200 is preferably beveled, as are lateral members 1206. Because these members are beveled, they include a plurality of edges and faces that facilitate alignment during insertion as well as facilitate a tight fit of carrier 1200 within socket 132. Leading edge base 1212 provides structural rigidity for lateral members 1206 and central member 1207. FIG. 12B is a diagram illustrating a bottom view of carrier 1200 according to one preferred embodiment of the invention. As illustrated in FIG. 12B, lateral members 1206, cross member 1207 and leading edge base 1212 provide a frame around a chip cavity 1236. It is chip cavity 1236 in which ROM chip 136 is disposed. In one preferred embodiment, ROM chip 136 is mounted on a relatively flat structure such as a printed circuit board. An example implementation of this embodiment is illustrated in FIG. 14. As illustrated in FIG. 14, ROM chip 136 is mounted on a printed circuit board 1404. A printed circuit board 1404 includes a plurality of contacts 1408 that are used to make electrical contact with corresponding contacts in socket 132. Leads 1406 are used to connect the leads of ROM chip 136 with contacts 1408.

In one embodiment, contacts in socket 132 (not illustrated) are implemented using wiper contacts similar, for example, to those found in phone jacks or circuit board card-edge connectors. To maintain solid electrical contact, the wiper contacts can be spring loaded using, for example springs, or the sprung force of the bent contact metal itself. The contacts in socket 132 as well as contacts 1408 and leads 1406 are implemented using a conductive material, such as, for example, copper, gold, silver or other conductive material.

The width and thickness of contacts in socket 132, leads 1406 and contacts 1408 as disposed on printed circuit board 1404 can be varied to provide the proper amount of conductivity depending on the implementation. Additionally, the area and thickness provided for a ground plane or ground lead 146 is chosen to provide adequate current handling capacity for grounding.

Printed circuit board 1404 in one embodiment includes tabs 1412. Tabs 1412 align with recesses 1214 to facilitate placement of ROM chip 136 and circuit board 1404 within chip cavity 1236. A flexible tab 1234 holds printed circuit board 1404 in place. A crenelated or other structure 1242 can also be provided to help hold circuit board 1404 in place. Structure 1242 can be crenelated as illustrated in FIG. 12B, a contiguous structure, or some other alternative structure. The combination of structure 1242 and tab 1234 allows circuit board 1404 to be slid under structure 1242 and snapped into place below an edge of tab 1234. A ridge 1244 extending around or partially around the interior of chip cavity 1236 provides a support on which printed circuit board 1404 can rest. The combination of ridge 1244 in conjunction with structure 1242 and tab 1234 holds circuit board 1404 firmly in place within chip cavity 1236. In one embodiment, a recess 1237 is provided as an artifact of the molding process.

Figure 15:
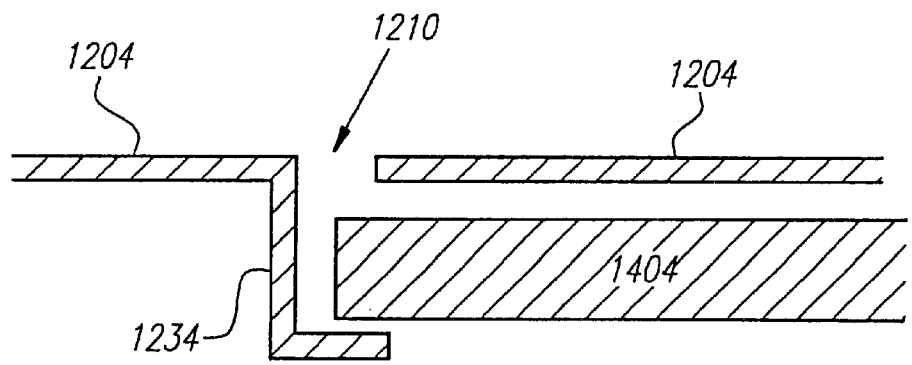
FIG. 15 is a diagram illustrating a cross-sectional view of a slot and tab according to one embodiment of the invention.

Chip carrier 1200 can be implemented using a molded acrylonitrile butadiene styrene polymer (ABS), a polyoxymethlyene (POM) polymer, a styrene polymer or styrene copolymers. In one embodiment, tab 1234 extends from slot 1210 to facilitate the flexibility of tab 1234 for insertion and removal of printed circuit board 1404. FIG. 15 is a diagram illustrating a cross-sectional view of slot 1210 and tab 1234. As illustrated, in this embodiment, tab 1234 is molded as portion of top base 1204. The presence of slot 1210 provides additional flexibility to tab 1234 without stressing the area where tab 1234 meets top surface 1204. Also illustrated in FIG. 15 is the interface between tab 1234, the bottom surface of top face 1204, and printed circuit board 1404.

Figure 13:
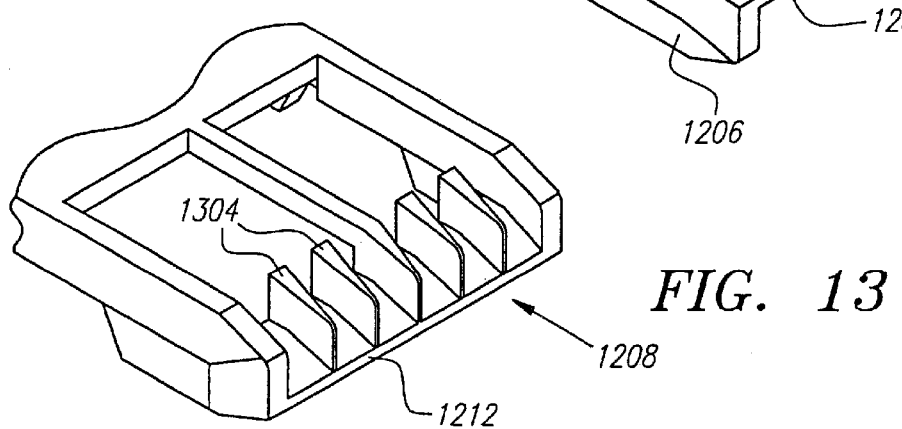
FIG. 13 is a diagram illustrating in more detail one embodiment of a leading edge of the chip carrier illustrated in FIG. 12.

FIG. 13 is a diagram illustrating in more detail one embodiment of leading edge 1208. In this embodiment, a plurality of teeth 1304 are disposed on leading edge base 1212. These teeth 1304 can be implemented to facilitate guidance of chip carrier 1200 into socket 132. In the embodiment illustrated in FIG. 13, teeth 1304 are implemented as truncated right prisms or pyramidal frustrums. Alternative shapes can be implemented, however, the angled leading edge of teeth 1304 facilitates guidance of carrier 1200. Additionally, in the embodiment illustrated in FIG. 13, teeth 1304 do not extend beyond leading edge base 1212. In this embodiment, teeth 1304 do not extend between contacts 1408 on printed circuit board 1404.

The various embodiments of the invention described above may be implemented using hardware, software or a combination thereof and may be implemented in a computer system or other processing system. In fact, in one embodiment, these elements are implemented using a computer system capable of carrying out the functionality described with respect thereto. An example computer system is such as that illustrated in FIG. 1.

Figure 16:
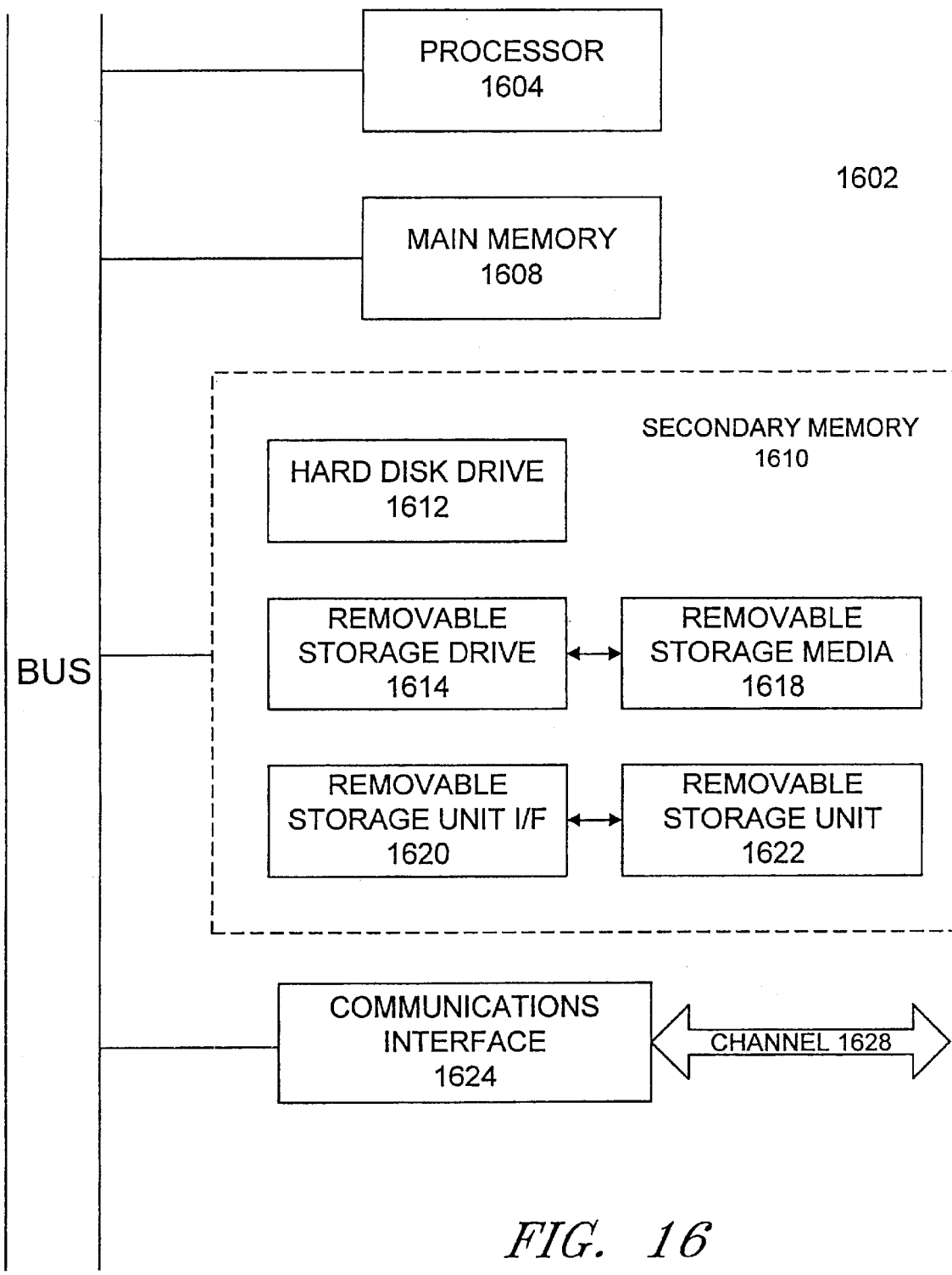
FIG. 16 is a block diagram illustrating an example computer system in which elements and functionality of the invention are implemented according to one embodiment of the invention.

FIG. 16 is a block diagram illustrating a general purpose computer system, including examples of computer readable media for providing computer software or instructions to perform the functionality described herein. The illustrated computer system 1602 includes one or more processors, such as processor 1604. The processor 1604 is connected to a communication bus 1606. Various software embodiments are described in terms of this example computer system. After reading this description, it will become apparent to a person skilled in the relevant art how to implement the invention using other computer systems or computer architectures, including, for example, the architecture illustrated in FIG. 1.

Computer system 1602 also includes a main memory 1608, preferably random access memory (RAM), and can also include a secondary memory 1610. The secondary memory 1610 can include, for example, a hard disk drive 1612 and/or a removable storage drive 1614, representing a floppy disk drive, a magnetic tape drive, an optical disk drive, etc. Removable storage drive 1614 reads from and/or writes to a removable storage medium 1618. Removable storage media 1618, represents a floppy disk, magnetic tape, optical disk, etc. which is read by and written to by removable storage drive 1614. As will be appreciated, the removable storage media 1618 includes a computer-usable storage medium having stored therein computer software and/or data.

In alternative embodiments, secondary memory 1610 may include other similar means for allowing computer programs or other instructions to be loaded into computer system 1602. Such means can include, for example, a removable storage unit 1622 and an interface 1620. Examples of such can include a program cartridge and cartridge interface (such as, for example, that found in video game devices), a removable memory chip (such as, for example, an EPROM, PROM or other memory device) and associated socket, and other removable storage units 1622 and interfaces 1620 which allow software and data to be transferred from the removable storage unit 1622 to computer system 1602. In some embodiments, removable storage unit 1622. may be affixed permanently to removable storage unit interface 1520.

Computer system 1602 can also include a communications interface 1624. Communications interface 1624 allows software and data to be transferred between computer system 1602 and external devices. Examples of communications interface 1624 can include a modem, a network interface (such as an Ethernet card), a communications port, a PCMCIA slot and card, etc. Software ad data transferred via communications interface 1624 are in the form of signals which can be electronic, electromagnetic, optical or other signals capable of being received by communications interface 1624. These signals are provided to communications interface via a channel 1628. This channel 1628 carries signals and can be implemented using a wireless medium, wire or cable, fiber optics, or other communications medium. Some examples of a channel can include a phone line, a cellular phone link, an RF link, a network, the Internet, and other communications channels.

In this document, the terms "computer program medium" and "computer usable medium" are used to generally refer to media such as removable storage media 1618, a hard disk installed in hard disk drive 1612, removable storage unit 1622 and signals on channel 1628. These terms can also refer to main memory 1608 where memory 1608 stores a computer program or a part thereof. These computer program products are means for providing software to computer system 1602.

Computer programs or instructions (also called computer control logic) can be stored in main memory 1608 and/or secondary memory 1610. Computer programs can also be received via communications interface 1624. Such computer programs, when executed, enable the computer system 1602 to perform the features of the present invention as discussed herein. In particular, the computer programs, when executed, enable the processor 1604 to perform the features of the present invention. Accordingly, such computer programs represent controllers of the computer system 1602.

In an embodiment where the elements are implemented using software, the software may be stored in a computer program product and loaded into computer system 1602 using removable storage drive 1614, removable storage unit 1622, hard drive 1612 or communications interface 1624. The control logic (software), when executed by the processor 1604, causes the processor 1604 to perform the functions of the invention as described herein.

In another embodiment, the elements are implemented primarily in hardware using, for example, hardware components such as application specific integrated circuits (ASICs). Implementation of the hardware state machine so as to perform the functions described herein will be apparent to persons skilled in the relevant art(s). Although not a "computer program" in the traditional sense, the hardware components can be thought of as a computer program medium (albeit, perhaps hard-wired) which enables the system to perform the described functions. In yet another embodiment, elements are implemented using a combination of both hardware and software. In this embodiment, the combination of the hardware and software can likewise be thought of as a computer program medium which enables the system to perform the described functions.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A ROM chip carrier for use with an assay device, the carrier comprising:

a body portion having a first end and a second end;

a rear tab, extending from said first end of said body potion;

first and second lateral members extending from said first end to said second end of said body portion, said first and second lateral members defining sides of said body portion and further forming boundaries of an open area within said body portion;

a leading edge, extending across said second end of said body portion from said first lateral member to said second lateral member;

a chip cavity, defined by said lateral members, said leading edge and a cross member extending across a central portion of said body portion from said first lateral member to said second lateral member;

a single central member extending across said open area in a direction from said leading edge toward said first end of said body portion;

a plurality of teeth disposed on said leading edge, wherein one dimension of said teeth is defined by a width of said leading edge.

2. The ROM chip carrier of claim 1, further comprising a printed circuit board, disposed in said chip cavity, said printed circuit board comprising a substrate and a plurality of contacts disposed on said substrate.

3. The ROM chip carrier of claim 2, wherein said lateral members each comprise a recess and said printed circuit board comprises a pair of tabs which align with said recesses to facilitate placement of said circuit board within said chip cavity.

4. The ROM chip carrier of claim 2, further comprising a crenelated structure on said leading edge to hold said circuit board in place within said cavity.

5. The ROM chip carrier of claim 2, further comprising a tab mounted on said cross member to hold said circuit board in place within said cavity.

6. The ROM chip carrier of claim 2, wherein said contacts are gold.

7. The ROM chip carrier of claim 1, wherein said leading edge and said lateral members are beveled.

8. The ROM chip carrier of claim 1, wherein said chip carrier is made of one of the group of a molded acrylonitrile butadiene styrene polymer, a polyoxymethylene polymer, a styrene polymer or a styrene copolymer.

\* \* \* \* \*